(12) United States Patent
Schieweck et al.

(10) Patent No.: US 7,320,975 B2
(45) Date of Patent: Jan. 22, 2008

(54) 2-(2-PYRIDYL)-5-PHENYL-6-AMINO-PYRIMIDINE, METHOD AND INTERMEDIATE PRODUCTS FOR THE PRODUCTION AND USE THEREOF FOR COMBATING NOXIOUS FUNGI

(75) Inventors: Frank Schieweck, Hessheim (DE); Jordi Tormo i Blasco, Limburgerhof (DE); Thomas Grote, Wachenheim (DE); Andreas Gypser, Mannheim (DE); Bernd Müller, Frankenthal (DE); Joachim Rheinheimer, Ludwigshafen (DE); Ingo Rose, Mannheim (DE); Peter Schäfer, Ottersheim (DE); Wassilios Grammenos, Ludwigshafen (DE); Markus Gewehr, Kastellaun (DE); Anja Schwögler, Mannheim (DE); Carsten Blettner, Ludwigshafen (DE); Eberhard Ammermann, Heppenheim (DE); Siegfried Strathmann, Limburgerhof (DE); Gisela Lorenz, Hambach (DE); Reinhard Stierl, Mutterstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 530 days.

(21) Appl. No.: 10/505,146

(22) PCT Filed: Feb. 6, 2003

(86) PCT No.: PCT/EP03/01162
§ 371 (c)(1),
(2), (4) Date: Aug. 20, 2004

(87) PCT Pub. No.: WO03/070721
PCT Pub. Date: Aug. 28, 2003

(65) Prior Publication Data
US 2005/0107401 A1 May 19, 2005

(30) Foreign Application Priority Data
Feb. 21, 2002 (DE) ............................ 102 07 428
Mar. 8, 2002 (DE) ............................ 102 10 136

(51) Int. Cl.
*C07D 401/04* (2006.01)
*A01N 43/54* (2006.01)
(52) U.S. Cl. .................. 514/235.8; 514/256; 544/122; 544/319; 544/328; 544/333
(58) Field of Classification Search ................ 544/122, 544/319, 328, 333; 514/235.8, 256
See application file for complete search history.

(56) References Cited
U.S. PATENT DOCUMENTS
5,250,530 A 10/1993 Giencke et al.

FOREIGN PATENT DOCUMENTS
EP 0 407 899 A2 1/1991

OTHER PUBLICATIONS
H.-J. Kabbe, "Substituierte 4-Hydroxy-und 4-Amino-Pyrimidine", Liebigs Annalen der Chemie., vol. 704, 1967, pp. 144-149.

*Primary Examiner*—Deepak Rao
(74) *Attorney, Agent, or Firm*—Rothwell, Figg, Ernst & Manbeck, P.C.

(57) ABSTRACT

The invention relates to 2-(2-pyridyl)-5-phenyl-6-aminopyrimidines of formula I, wherein the substitutes and the index have the following meaning: $R^1$ represents halogen, hydroxy, hyano, hxo, nitro, amino, mercapto, alkyl, halogenalkyl, alkenyl, alkinyl, cycloalkyl, alkoxy, halogenalkoxy, carboxyl, alkoxycarbonyl, carbamoyl, alkylaminocarbonyl, dialkylamincarbonyl, morpholinocarbonyl, pyrrolidinocarbonyl, alkylcarbonylamino, alkylamino. dialkylamino, alkylthio, alkylsulfinyl, alkylsulfonyl, hydroxysulfonyl, aminosulfonyl, alkylaminosulfonyl, dialkylaminosulfonyl; m=0 or 1-4; $R^2$ represents hydrogen, halogen, cyano, alkyl, halogenalkyl or alkoxy; $R^3$, $R^4$ represents hydrogen, alkyl, halogenalkyl, cycloalkyl, halogencycloalkyl, alkenyl, halogenalkenyl, cycloalkenyl, alkinyl, halogenalkinyl or cycloalkinyl, $R^3$ and $R^4$ together with the nitrogen atom to which they are connected, form a five or six-membered ring which is interrupted by an atom from the group O, N or S and/or can be substituted according to the description; $R^5$ represents halogen, alkyl or halogenalkyl; $R^6$ represents hydrogen or one of the known groups in $R^5$; $R^7$, $R^8$ represent hydrogen, halogen, alkyl or halogenalkyl; $R^9$ represents hydrogen, halogen, hydroxy, cyano, alkyl, alkoxy, cycloalkoxy, halogenalkoxy, alkoxycarbonyl or alkylaminocarbonyl. The invention also relates to a method and intermediate product for the production of said compound in addition to the use thereof for combating undesirable plants

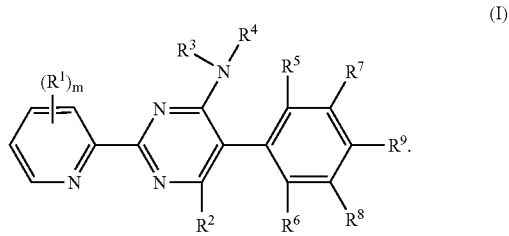

(I)

22 Claims, No Drawings

2-(2-PYRIDYL)-5-PHENYL-6-AMINO-PYRIMIDINE, METHOD AND INTERMEDIATE PRODUCTS FOR THE PRODUCTION AND USE THEREOF FOR COMBATING NOXIOUS FUNGI

CROSS REFERENCE TO RELATED APPLICATION

This application is a 35 USC § 371 National Phase Entry Application from PCT/EP03/01162, filed Feb. 6, 2003, and designating the U.S.

The present invention relates to 2-(2-pyridyl)-5-phenyl-6-aminopyrimidines of the formula I,

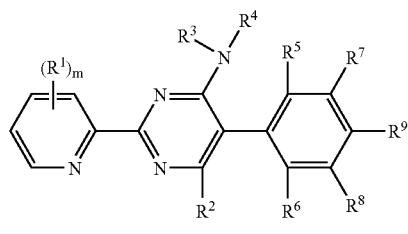

in which the substituents and the subscript have the following meanings:

$R^1$ is halogen, hydroxyl, cyano, oxo, nitro, amino, mercapto, $C_1$-$C_6$-alkyl, $C_1$-$C_6$-haloalkyl, $C_2$-$C_6$-alkenyl, $C_2$-$C_6$-alkynyl, $C_3$-$C_6$-cycloalkyl, $C_1$-$C_6$-alkoxy, $C_1$-$C_6$-haloalkoxy, carboxyl, $C_1$-$C_7$-alkoxycarbonyl, carbamoyl, $C_1$-$C_7$-alkylaminocarbonyl, $C_1$-$C_6$-alkyl-$C_1$-$C_6$-alkylaminocarbonyl, morpholinocarbonyl, pyrrolidinocarbonyl, $C_1$-$C_7$-alkylcarbonylamino, $C_1$-$C_6$-alkylamino, di($C_1$-$C_6$-alkyl)amino, $C_1$-$C_6$-alkylthio, $C_1$-$C_6$-alkylsulfinyl, $C_1$-$C_6$-alkylsulfonyl, hydroxysulfonyl, aminosulfonyl, $C_1$-$C_6$-alkylaminosulfonyl or di($C_1$-$C_6$-alkyl) aminosulfonyl;

m is 0, 1, 2, 3 or 4;

$R^2$ is hydrogen, halogen, cyano, $C_1$-$C_6$-alkyl, $C_1$-$C_6$-haloalkyl or $C_1$-$C_6$-alkoxy;

$R^3$, $R^4$ independently of one another, are hydrogen, $C_1$-$C_6$-alkyl, $C_1$-$C_6$-haloalkyl, $C_3$-$C_6$-cycloalkyl, $C_3$-$C_6$-halocycloalkyl, $C_2$-$C_6$-alkenyl, $C_2$-$C_6$-haloalkenyl, $C_3$-$C_6$-cycloalkenyl, $C_2$-$C_6$-alkynyl, $C_2$-$C_6$-haloalkynyl or $C_3$-$C_6$-cycloalkynyl, $R^3$ and $R^4$ can also, together with the nitrogen atom to which they are bonded, form a five- or six-membered ring which may be interrupted by an atom from the group consisting of O, N and S and/or may carry one or more substituents from the group consisting of halogen, $C_1$-$C_6$-alkyl, $C_1$-$C_6$-haloalkyl or oxy-$C_1$-$C_3$-alkylenoxy or in which two adjacent carbon atoms or one N— and one neighboring carbon atom can be connected via a $C_1$-$C_4$-alkylene chain;

$R^5$ is halogen, $C_1$-$C_6$-alkyl or $C_1$-$C_6$-haloalkyl;

$R^6$ is hydrogen or one of the groups mentioned under $R^5$;

$R^7$, $R^8$ independently of one another, are hydrogen, halogen, $C_1$-$C_6$-alkyl or $C_1$-$C_6$-haloalkyl;

$R^9$ is hydrogen, halogen, hydroxyl, cyano, $C_1$-$C_6$-alkyl, $C_1$-$C_6$-alkoxy, $C_3$-$C_6$-cycloalkoxy, $C_1$-$C_6$-haloalkoxy, $C_1$-$C_6$-alkoxycarbonyl or $C_1$-$C_6$-alkylaminocarbonyl.

The invention also relates to processes for and intermediates in the preparation of these compounds and to the use thereof in the control of harmful fungi.

2-Pyridylaminopyrimidine derivatives with a fungicidal effect are generally known from EP-A 407 899. They are suitable as plant protection agents against harmful fungi.

However, in many cases, their action is unsatisfactory. It is therefore an object of the present invention to find compounds with improved activity.

The phenylpyrimidine derivatives I defined at the start were accordingly found. Processes for and intermediates in their preparation, preparations comprising them for the control of harmful fungi and the use thereof for this purpose were also found.

The compounds of the formula I have, in comparison with the known compounds, an increased effectiveness against harmful fungi.

The compounds I are distinguished from the known compounds through the substitution of the 5-phenyl ring, in which at least one ortho-substituent is not hydrogen.

Compounds of formula I are accessible, for example, according to the following synthetic route,

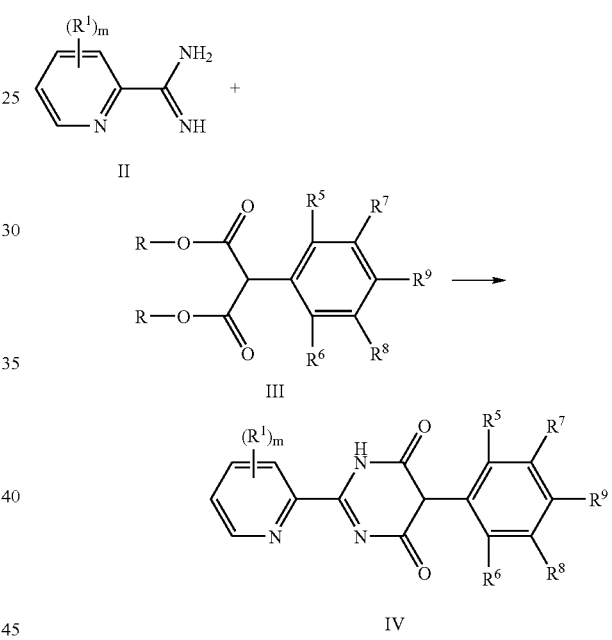

in which, in formula III, R is $C_1$-$C_6$-alkyl. The reaction usually takes place in a protic solvent, such as, e.g., alcohols, especially ethanol. However, it can also be carried out in aprotic solvents, such as, e.g., pyridine, N,N-dimethylformamide, N,N-dimethylacetamide, or mixtures thereof. The reaction is usually carried out at 50 to 250° C., preferably at 100 to 200° C. [cf.: Austr. J. Chem., Vol. 32, pp. 669-679 (1979); J. Org. Chem., Vol. 58, pp. 3785-3786 (1993); Arm. Xim. ZH, Vol. 38, N11, 718-719 (1985)].

As a rule, it is advantageous to operate in the presence of a base, which can be used in equimolar amounts or also in excess. Alkali metal and alkaline earth metal alkoxides, such as sodium methoxide, sodium ethoxide, potassium ethoxide or potassium tert-butoxide, especially sodium ethoxide, or also nitrogenous bases, such as triethylamine, triisopropylethylamine and N-methylpiperidine, especially pyridine and tributylamine, are possible as bases.

The components are usually used in approximately stoichiometric amounts. However, it can also be advantageous to use one of the components in excess.

The starting materials of the formulae II and III are known in the literature [cf. EP-A 588 146; EP-A 1 002 788; WO-A 98/41496], some are also commercially available or can be prepared according to the cited literature.

Compounds IV are converted to the dichloropyrimidines of the formula V [cf. U.S. Pat. No. 4,963,678; EP-A 745 593; DE-A 196 42 533; WO-A 99/32458; J. Org. Chem., Vol. 58, pp. 3785-3786 (1993); Helv. Chim. Acta, Vol. 64, pp. 113-152 (1981)].

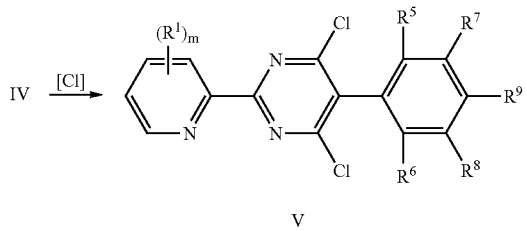

$POCl_3$, $PCl_3/Cl_2$ or $PCl_5$, or mixtures of these reagents, for example, are suitable as chlorinating agent [Cl]. The reaction can be carried out in excess chlorinating agent ($POCl_3$) or an inert solvent, such as, for example, acetonitrile or 1,2-dichloroethane. It is preferable to carry out the reaction in $POCl_3$.

This reaction usually takes place between 10 and 180° C. For practical reasons, the reaction temperature usually corresponds to the boiling temperature of the chlorinating agent ($POCl_3$) or of the solvent used. The process is advantageously carried out with the addition of N,N-dimethylformamide, in catalytic or substoichiometric amounts, or of nitrogenous bases, such as, for example, N,N-dimethylaniline.

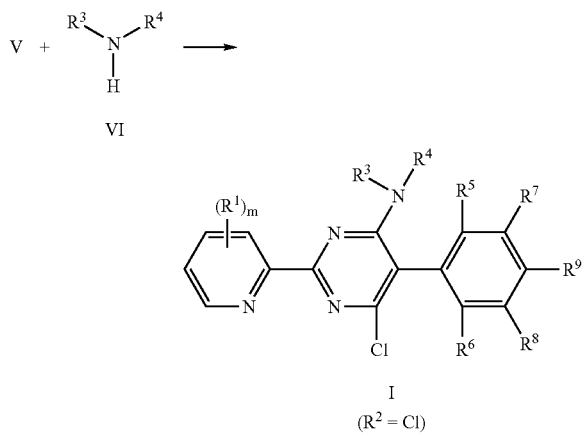

The dichlorinated compounds of the formula V are converted to the compounds of the formula I, in which $R^2$ is chlorine, by amination with VI.

This reaction is usually carried out at 0 to 150° C., preferably at 20 to 120° C. [cf. J. Chem. Res. S (7), pp. 286-287 (1995), Liebigs Ann. Chem., pp. 1703-1705 (1995)] in an inert solvent, optionally in the presence of an auxiliary base.

Protic solvents, such as alcohols, for example, ethanol, or aprotic solvents, such as aromatic hydrocarbons or ethers, for example toluene, o-, m- and p-xylene, diethyl ether, diisopropyl ether, tert-butyl methyl ether, dioxane or tetrahydrofuran, in particular tert-butyl methyl ether or tetrahydrofuran, are possible as solvents. $NaHCO_3$, $Na_2CO_3$, $Na_2HPO_4$, $Na_2B_4O_7$, diethylaniline or ethyldiisopropylamine, for example, is suitable as auxiliary base.

The components are generally used in an approximately stoichiometric ratio. However, it can be advantageous to use the amine in excess.

The amines of the formula VI are commercially available or are known in the literature or can be prepared according to known methods.

Compounds of the formula I in which $R^2$ is alkoxy are obtained from the corresponding chlorinated compounds of the formula I in which $R^2$ is chlorine by reaction with alkali metal or alkaline earth metal alkoxides [cf.: Heterocycles, Vol. 32, pp. 1327-1340 (1991); J. Heterocycl. Chem., Vol. 19, pp. 1565-1567 (1982); Geterotsikl. Soedin, pp. 400-402 (1991)].

Compounds of the formula I in which $R^2$ is cyano are obtained from the corresponding chlorinated compounds of the formula I ($R^2$=Cl) by reaction with alkali metal, alkaline earth metal or metal cyanides, such as NaCN, KCN or $Zn(CN)_2$ [cf.: Heterocycles, Vol. 39, pp. 345-356 (1994); Collect. Czech. Chem. Commun., Vol. 60, pp. 1386-1389 (1995); Acta Chim. Scand., Vol. 50, pp. 58-63 (1996)].

Compounds of the formula I in which $R^2$ is hydrogen are obtained from the corresponding chlorinated compounds of the formula I ($R^2$=Cl) by catalytic hydrogenation [cf.: J. Fluorine Chem., Vol. 45, pp. 417-430 (1989); J. Heterocycl. Chem., Vol. 29, pp. 1369-1370 (1992)] or by reduction with zinc in acetic acid [cf.: Org. Prep. Proced. Int., Vol. 27, pp. 600-602 (1995); JP-A 09/165 379].

Compounds of the formula I in which $R^2$ is $C_1$-$C_6$-alkyl or $C_1$-$C_6$-haloalkyl (formula Ia) can be prepared, analogously to the synthetic sequence described for the compounds I in which $R^2$ is chlorine, by suitable modification of the starting materials of the formula III. Instead of the phenylmalonic esters of the formula III, phenyl-β-ketoesters of the formula VII in which $R^2$ represents alkyl or haloalkyl are used with the amidine of the formula II. The following reactions are carried out analogously to the syntheses described above for the compounds with $R^2$=chlorine.

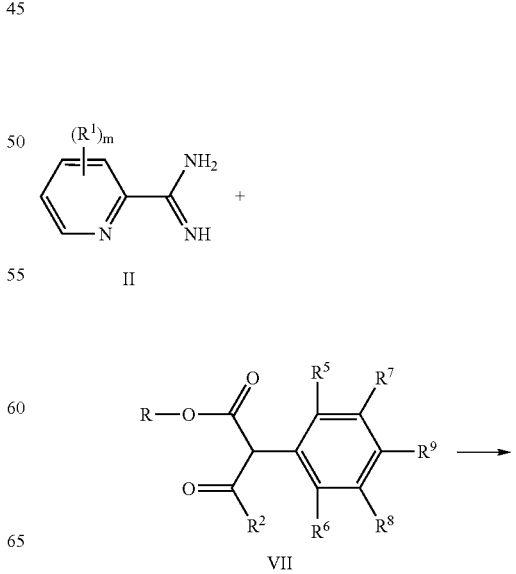

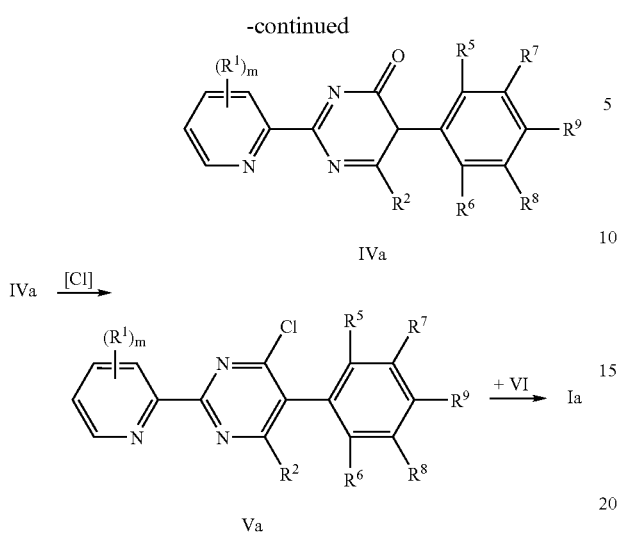

The compounds of the formulae IVa and Va are novel.

The reaction mixtures are worked up conventionally, e.g. by mixing with water, separating the phases and possibly chromatographic purification of the crude products. Some of the intermediates and final products are obtained in the form of colorless or slightly brownish viscous oils which, under reduced pressure and at moderately elevated temperature, are freed or purified from volatile constituents. Provided that the intermediates and final products are obtained as solids, the purification can also take place by recrystallization or trituration.

If individual compounds I are not accessible by the routes described above, they can be prepared by derivatization of other compounds I.

Collective terms were used in the definitions of the symbols given in the above formulae, which collective terms are generally representative of the following substituents:

halogen: fluorine, chlorine, bromine and iodine;

alkyl: saturated, straight-chain or branched hydrocarbon radicals with 1 to 4, 6 or 8 carbon atoms, e.g. $C_1$-$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

haloalkyl: straight-chain or branched alkyl groups with 1 to 8 carbon atoms (as mentioned above), in which the hydrogen atoms in these groups can be partially or completely replaced by halogen atoms as mentioned above, e.g. $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl;

alkenyl: unsaturated, straight-chain or branched hydrocarbon radicals with 2 to 4, 6 or 8 carbon atoms and a double bond in any position, e.g. $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-2-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkynyl: straight-chain or branched hydrocarbon groups with 2 to 4, 6 or 8 carbon atoms and a triple bond in any position, e.g. $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

cycloalkyl: saturated monocyclic hydrocarbon groups with 3 to 6 carbon ring members, such as cyclopropyl, cyclobutyl, cyclopentyl and cyclohexyl;

alkoxycarbonyl: an alkoxy group with 1 to 6 carbon atoms (as mentioned above) which is bonded to the backbone via a carbonyl group (—CO—);

oxyalkylenoxy: unbranched divalent chains formed from 1 to 3 $CH_2$ groups in which both valences is bonded to the backbone via an oxygen atom, e.g. $OCH_2O$, $OCH_2CH_2O$ and $OCH_2CH_2CH_2O$.

The embodiments of the intermediates which are especially preferred with regard to the variables correspond to those of the radicals $R^1$ to $R^9$ of the formula I.

In view of their intended use of the 2-pyridylpyrimidines of the formula I, the following meanings of the substituents, in each case alone or in combination, are especially preferred:

Special preference is given to compounds I in which m=0.

Preference is also given to compounds I in which m=1 or 2 and $R^1$ has the following meaning:

halogen, hydroxyl, cyano, nitro, amino, mercapto, $C_1$-$C_6$-alkyl, $C_1$-$C_6$-haloalkyl, $C_2$-$C_6$-alkenyl, $C_2$-$C_6$-alkynyl, $C_3$-$C_6$-cycloalkyl, $C_1$-$C_6$-alkoxy, $C_1$-$C_6$-haloalkoxy, carboxyl, $C_1$-$C_7$-alkoxycarbonyl, carbamoyl, $C_1$-$C_7$-alkylaminocarbonyl, $C_1$-$C_6$-alkyl-$C_1$-$C_6$-alkylaminocarbonyl, morpholinocarbonyl, pyrrolidinocarbonyl, $C_1$-$C_7$-alkylcarbonylamino, $C_1$-$C_6$-alkylamino, di($C_1$-$C_6$-alkyl)amino, $C_1$-$C_6$-alkylthio, $C_1$-$C_6$-alkylsulfinyl, $C_1$-$C_6$-alkylsulfonyl, hydroxysulfonyl, aminosulfonyl, $C_1$-$C_6$-alkylaminosulfonyl or di($C_1$-$C_6$-alkyl) aminosulfonyl.

Particular preference is given to compounds I in which $R^1$ is selected from the group:

halogen, cyano, nitro, amino, $C_1$-$C_6$-alkyl, $C_1$-$C_6$-haloalkyl, $C_1$-$C_6$-alkoxy, carboxyl, $C_1$-$C_7$-alkoxycarbonyl, carbamoyl, $C_1$-$C_7$-alkylaminocarbonyl, di($C_1$-$C_6$-alkyl)aminocarbonyl or $C_1$-$C_7$-alkylcarbonylamino.

Preference is furthermore given to compounds I in which m is 1 and $R^1$ is halogen, cyano, nitro, methyl or methoxy.

Particular preference is given to compounds I in which $R^1$ is fluorine, chlorine or methyl.

Preference is given to compounds I in which $R^2$ is halogen, $C_1$-$C_6$-alkyl or $C_1$-$C_6$-alkoxy, in particular halogen.

Special preference is given to compounds of the formula I in which $R^2$ represents chlorine.

In addition, preference is given to compounds of the formula I in which $R^3$ is hydrogen.

Special preference is similarly given to compounds I in which $R^3$ and $R^4$ represent, independently of one another, $C_1$-$C_6$-alkyl, $C_1$-$C_6$-haloalkyl, $C_3$-$C_6$-cycloalkyl or $C_2$-$C_6$-alkenyl.

Particular preference is given to compounds of the formula I in which $R^3$ is hydrogen and $R^4$ is $C_1$-$C_4$-haloalkyl.

Furthermore, preference is given to compounds I in which $R^3$ and $R^4$, together with the nitrogen atom to which they are bonded, form a five- or six-membered ring which can be interrupted by a heteroatom and can carry one or two $C_1$-$C_6$-alkyl substituents.

Special preference is similarly given to compounds I in which $R^5$ represents halogen or methyl and $R^6$ represents hydrogen.

Special preference is given to compounds I in which $R^6$ represents hydrogen.

Special preference is furthermore given to compounds I in which $R^7$ and $R^8$ are identical or different and represent hydrogen or halogen.

Special preference is also given to compounds I in which $R^9$ is hydrogen, halogen, $C_1$-$C_4$-alkyl, $C_1$-$C_4$-alkoxy, $C_1$-$C_6$-alkoxycarbonyl or $C_1$-$C_6$-alkylaminocarbonyl.

Special preference is similarly given to compounds I' in which $R^1$ to $R^4$ are defined as for formula I and $R^A$ is the following radical combinations: 2-methyl-4-fluoro, 2-fluoro-4-methyl, 2,4-dimethyl, 2-chloro-6-fluoro, 2,6-difluoro, 2,6-dichloro, 2-methyl-6-fluoro, 2,4,6-trifluoro, 2,6-difluoro-4-methoxy and pentafluoro.

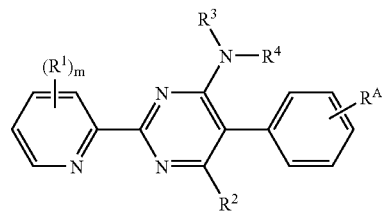

I'

Special preference is given, over and above that, to compounds of the formula I' in which $R^A$ represents 2,4,6-trifluoro.

Particular preference is given, in view of their use, to the compounds I compiled in the following tables. The groups mentioned in the tables for a substituent additionally represent, considered per se, independently of the combination in which they are mentioned, a particularly preferred form of the substituent in question.

TABLE 1

Compounds of the formula I-1 in which $R^5$ is fluorine, $R^6$ is chlorine and $R^7$, $R^8$ and $R^9$ are hydrogen and the combination of the radicals $R^3$ and $R^4$ for a compound each time corresponds to a row of table A

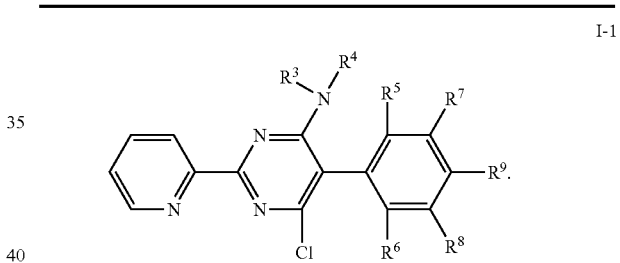

I-1

Table 2

Compounds of the formula I-1 in which $R^5$ and $R^6$ are fluorine and $R^7$, $R^8$ and $R^9$ are hydrogen and the combination of the radicals $R^3$ and $R^4$ for a compound each time corresponds to a row of table A Table 3

Compounds of the formula I-1 in which $R^5$ and $R^6$ are chlorine and $R^7$, $R^8$ and $R^9$ are hydrogen and the combination of the radicals $R^3$ and $R^4$ for a compound each time corresponds to a row of table A Table 4

Compounds of the formula I-1 in which $R^5$ is fluorine and $R^6$ is methyl and $R^7$, $R^8$ and $R^9$ are hydrogen and the combination of the radicals $R^3$ and $R^4$ for a compound each time corresponds to a row of table A Table 5

Compounds of the formula I-1 in which $R^5$, $R^6$ and $R^9$ are fluorine and $R^7$ and $R^8$ are hydrogen and the combination of the radicals $R^3$ and $R^4$ for a compound each time corresponds to a row of table A Table 6

Compounds of the formula I-1 in which $R^5$ and $R^6$ are fluorine, $R^7$ and $R^8$ are hydrogen and $R^9$ is methoxy and the combination of the radicals $R^3$ and $R^4$ for a compound each time corresponds to a row of table A Table 7

Compounds of the formula I-1 in which $R^5$, $R^6$, $R^7$, $R^8$ and $R^9$ are fluorine and the combination of the radicals $R^3$ and $R^4$ for a compound each time corresponds to a row of table A Table 8

Compounds of the formula I-1 in which $R^5$ is methyl, $R^6$, $R^7$ and $R^8$ are hydrogen and $R^9$ is fluorine and the combination of the radicals $R^3$ and $R^4$ for a compound each time corresponds to a row of table A Table 9

Compounds of the formula I-1 in which $R^5$ is fluorine, $R^6$, $R^7$ and $R^8$ are hydrogen and $R^9$ is methyl and the combination of the radicals $R^3$ and $R^4$ for a compound each time corresponds to a row of table A Table 10

Compounds of the formula I-1 in which $R^5$ and $R^9$ are methyl and $R^6$, $R^7$ and $R^8$ are hydrogen and the combination of the radicals $R^3$ and $R^4$ for a compound each time corresponds to a row of table A Table 11

Compounds of the formula I-1 in which $R^5$ and $R^6$ are fluorine, $R^7$ and $R^8$ are hydrogen and $R^9$ is hydroxyl and the combination of the radicals $R^3$ and $R^4$ for a compound each time corresponds to a row of table A

TABLE A

| No. | $R^3$ | $R^4$ |
|---|---|---|
| A-1 | CH$_2$CH$_3$ | H |
| A-2 | CH$_2$CH$_3$ | CH$_3$ |
| A-3 | CH$_2$CH$_3$ | CH$_2$CH$_3$ |
| A-4 | CH$_2$CH$_2$CH$_3$ | H |
| A-5 | CH$_2$CH$_2$CH$_3$ | CH$_3$ |
| A-6 | CH$_2$CH$_2$CH$_3$ | CH$_2$CH$_3$ |
| A-7 | CH$_2$CH$_2$CH$_3$ | CH$_2$CH$_2$CH$_3$ |
| A-8 | CH$_2$—CH$_2$F | H |
| A-9 | CH$_2$—CH$_2$F | CH$_3$ |
| A-10 | CH$_2$—CH$_2$F | CH$_2$CH$_3$ |
| A-11 | CH$_2$CF$_3$ | H |
| A-12 | CH$_2$CF$_3$ | CH$_3$ |
| A-13 | CH$_2$CF$_3$ | CH$_2$CH$_3$ |
| A-14 | CH$_2$CF$_3$ | CH$_2$CH$_2$CH$_3$ |
| A-15 | CH$_2$CCl$_3$ | H |
| A-16 | CH$_2$CCl$_3$ | CH$_3$ |
| A-17 | CH$_2$CCl$_3$ | CH$_2$CH$_3$ |
| A-18 | CH$_2$CCl$_3$ | CH$_2$CH$_2$CH$_3$ |
| A-19 | CH(CH$_3$)$_2$ | H |
| A-20 | CH(CH$_3$)$_2$ | CH$_3$ |
| A-21 | CH(CH$_3$)$_2$ | CH$_2$CH$_3$ |
| A-22 | CH(CH$_3$)$_2$ | CH$_2$CH$_2$CH$_3$ |
| A-23 | CH$_2$C(CH$_3$)$_3$ | H |
| A-24 | CH$_2$C(CH$_3$)$_3$ | CH$_3$ |
| A-25 | CH$_2$C(CH$_3$)$_3$ | CH$_2$CH$_3$ |
| A-26 | CH$_2$CH(CH$_3$)$_2$ | H |
| A-27 | CH$_2$CH(CH$_3$)$_2$ | CH$_3$ |
| A-28 | CH$_2$CH(CH$_3$)$_2$ | CH$_2$CH$_3$ |
| A-29 | (±) CH(CH$_2$CH$_3$)CH$_3$ | H |
| A-30 | (±) CH(CH$_2$CH$_3$)CH$_3$ | CH$_3$ |
| A-31 | (±) CH(CH$_2$CH$_3$)CH$_3$ | CH$_2$CH$_3$ |
| A-32 | (R) CH(CH$_2$CH$_3$)CH$_3$ | H |
| A-33 | (R) CH(CH$_2$CH$_3$)CH$_3$ | CH$_3$ |
| A-34 | (R) CH(CH$_2$CH$_3$)CH$_3$ | CH$_2$CH$_3$ |
| A-35 | (S) CH(CH$_2$CH$_3$)CH$_3$ | H |
| A-36 | (S) CH(CH$_2$CH$_3$)CH$_3$ | CH$_3$ |

TABLE A-continued

| No. | $R^3$ | $R^4$ |
|---|---|---|
| A-37 | (S) CH(CH$_2$CH$_3$)CH$_3$ | CH$_2$CH$_3$ |
| A-38 | (±) CH(CH$_3$)—CH(CH$_3$)$_2$ | H |
| A-39 | (±) CH(CH$_3$)—CH(CH$_3$)$_2$ | CH$_3$ |
| A-40 | (±) CH(CH$_3$)—CH(CH$_3$)$_2$ | CH$_2$CH$_3$ |
| A-41 | (R) CH(CH$_3$)—CH(CH$_3$)$_2$ | H |
| A-42 | (R) CH(CH$_3$)—CH(CH$_3$)$_2$ | CH$_3$ |
| A-43 | (R) CH(CH$_3$)—CH(CH$_3$)$_2$ | CH$_2$CH$_3$ |
| A-44 | (S) CH(CH$_3$)—CH(CH$_3$)$_2$ | H |
| A-45 | (S) CH(CH$_3$)—CH(CH$_3$)$_2$ | CH$_3$ |
| A-46 | (S) CH(CH$_3$)—CH(CH$_3$)$_2$ | CH$_2$CH$_3$ |
| A-47 | (±) CH(CH$_3$)—C(CH$_3$)$_3$ | H |
| A-48 | (±) CH(CH$_3$)—C(CH$_3$)$_3$ | CH$_3$ |
| A-49 | (±) CH(CH$_3$)—C(CH$_3$)$_3$ | CH$_2$CH$_3$ |
| A-50 | (R) CH(CH$_3$)—C(CH$_3$)$_3$ | H |
| A-51 | (R) CH(CH$_3$)—C(CH$_3$)$_3$ | CH$_3$ |
| A-52 | (R) CH(CH$_3$)—C(CH$_3$)$_3$ | CH$_2$CH$_3$ |
| A-53 | (S) CH(CH$_3$)—C(CH$_3$)$_3$ | H |
| A-54 | (S) CH(CH$_3$)—C(CH$_3$)$_3$ | CH$_3$ |
| A-55 | (R) CH(CH$_3$)—C(CH$_3$)$_3$ | CH$_2$CH$_3$ |
| A-56 | (±) CH(CH$_3$)—CF$_3$ | H |
| A-57 | (±) CH(CH$_3$)—CF$_3$ | CH$_3$ |
| A-58 | (±) CH(CH$_3$)—CF$_3$ | CH$_2$CH$_3$ |
| A-59 | (R) CH(CH$_3$)—CF$_3$ | H |
| A-60 | (R) CH(CH$_3$)—CF$_3$ | CH$_3$ |
| A-61 | (R) CH(CH$_3$)—CF$_3$ | CH$_2$CH$_3$ |
| A-62 | (S) CH(CH$_3$)—CF$_3$ | H |
| A-63 | (S) CH(CH$_3$)—CF$_3$ | CH$_3$ |
| A-64 | (S) CH(CH$_3$)—CF$_3$ | CH$_2$CH$_3$ |
| A-65 | (±) CH(CH$_3$)—CCl$_3$ | H |
| A-66 | (±) CH(CH$_3$)—CCl$_3$ | CH$_3$ |
| A-67 | (±) CH(CH$_3$)—CCl$_3$ | CH$_2$CH$_3$ |
| A-68 | (R) CH(CH$_3$)—CCl$_3$ | H |
| A-69 | (R) CH(CH$_3$)—CCl$_3$ | CH$_3$ |
| A-70 | (R) CH(CH$_3$)—CCl$_3$ | CH$_2$CH$_3$ |
| A-71 | (S) CH(CH$_3$)—CCl$_3$ | H |
| A-72 | (S) CH(CH$_3$)—CCl$_3$ | CH$_3$ |
| A-73 | (S) CH(CH$_3$)—CCl$_3$ | CH$_2$CH$_3$ |
| A-74 | CH$_2$C(CH$_3$)=CH$_2$ | H |
| A-75 | CH$_2$C(CH$_3$)=CH$_2$ | CH$_3$ |
| A-76 | CH$_2$C(CH$_3$)=CH$_2$ | CH$_2$CH$_3$ |
| A-77 | cyclopentyl | H |
| A-78 | cyclopentyl | CH$_3$ |
| A-79 | cyclopentyl | CH$_2$CH$_3$ |
| A-80 | —(CH$_2$)$_4$— | |
| A-81 | (±) —(CH$_2$)$_2$—CH(CH$_3$)—CH$_2$— | |
| A-82 | (R) —(CH$_2$)$_2$—CH(CH$_3$)—CH$_2$— | |
| A-83 | (S) —(CH$_2$)$_2$—CH(CH$_3$)—CH$_2$— | |
| A-84 | —(CH$_2$)$_2$—CH(OCH$_3$)—CH$_2$— | |
| A-85 | —(CH$_2$)$_2$—CH(CH$_2$CH$_3$)—CH$_2$— | |
| A-86 | —(CH$_2$)$_2$—CH[CH(CH$_3$)$_2$]—CH$_2$— | |
| A-87 | —CH$_2$—CH=CH—CH$_2$— | |
| A-88 | —(CH$_2$)$_5$— | |
| A-89 | —(CH$_2$)$_2$—CH(CH$_3$)—(CH$_2$)$_2$— | |
| A-90 | (±) —(CH$_2$)$_3$—CH(CH$_3$)—CH$_2$— | |
| A-91 | (R)—(CH$_2$)$_3$—CH(CH$_3$)—CH$_2$— | |
| A-92 | (S)—(CH$_2$)$_3$—CH(CH$_3$)—CH$_2$— | |
| A-93 | —(CH$_2$)$_2$—C(O[CH$_2$]$_2$O)—(CH$_2$)$_2$— | |
| A-94 | —(CH$_2$)$_2$—C(O[CH$_2$]$_3$O)—(CH$_2$)$_2$— | |
| A-95 | 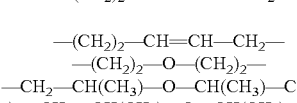 | |
| A-96 | —(CH$_2$)$_2$—CH=CH—CH$_2$— | |
| A-97 | —(CH$_2$)$_2$—O—(CH$_2$)$_2$— | |
| A-98 | —CH$_2$—CH(CH$_3$)—O—CH(CH$_3$)—CH$_2$— | |
| A-99 | (cis) —CH$_2$—CH(CH$_3$)—O—CH(CH$_3$)—CH$_2$— | |
| A-100 | (trans) —CH$_2$—CH(CH$_3$)—O—CH(CH$_3$)—CH$_2$— | |
| A-101 | —(CH$_2$)$_2$—NH—(CH$_2$)$_2$— | |
| A-102 | —(CH$_2$)$_2$—N(CH$_3$)—(CH$_2$)$_2$— | |
| A-103 | —(CH$_2$)$_2$—S—(CH$_2$)$_2$— | |
| A-104 | —(CH$_2$)$_2$—CHF—(CH$_2$)$_2$— | |
| A-105 | —(CH$_2$)$_3$—CHF—CH$_2$— | |

TABLE A-continued

| No. | R³ | R⁴ |
|-----|----|----|
| A-106 | | —(CH$_2$)$_2$—CH(CF$_3$)—(CH$_2$)$_2$— |
| A-107 | | —(CH$_2$)$_2$—CH(CH$_2$F)—(CH$_2$)$_2$— |
| A-108 | | —(CH$_2$)$_2$—CF$_2$—(CH$_2$)$_2$— |

The compounds I are suitable as fungicides. They are distinguished through an outstanding effectiveness against a broad spectrum of phytopathogenic fungi, especially from the classes of the Ascomycetes, Deuteromycetes, Phycomycetes and Basidiomycetes. Some are systemically effective and they can be used in plant protection as foliar and soil fungicides.

They are particularly important in the control of a multitude of fungi on various cultivated plants, such as wheat, rye, barley, oats, rice, maize, grass, bananas, cotton, soya, coffee, sugar cane, vines, fruits and ornamental plants, and vegetables, such as cucumbers, beans, tomatoes, potatoes and cucurbits, and on the seeds of these plants.

They are especially suitable for controlling the following plant diseases:

*Alternaria* species on fruit and vegetables,
*Botrytis cinerea* (gray mold) on strawberries, vegetables, ornamental plants and grapevines,
*Cercospora arachidicola* on peanuts,
*Erysiphe cichoracearum* and *Sphaerotheca fuliginea* on cucurbits,
*Blumeria graminis* (powdery mildew) on cereals,
*Fusarium* and *Verticillium* species on various plants,
*Helminthosporium* species on cereals,
*Mycosphaerella* species on bananas and peanuts,
*Phytophthora infestans* on potatoes and tomatoes,
*Plasmopara viticola* on grapevines,
*Podosphaera leucotricha* on apples,
*Pseudocercosporella herpotrichoides* on wheat and barley,
*Pseudoperonospora* species on hops and cucumbers,
*Puccinia* species on cereals,
*Pyricularia oryzae* on rice,
*Rhizoctonia* species on cotton, rice and lawns,
*Septoria nodorum* on wheat,
*Uncinula necator* on grapevines,
*Ustilago* species on cereals and sugar cane, and
*Venturia* species (scab) on apples and pears.

The compounds I are also suitable for controlling harmful fungi, such as *Paecilomyces variotii*, in the protection of materials (e.g. wood, paper, paint dispersions, fibers or fabrics) and in the protection of stored products.

The compounds I are employed by treating the fungi or the plants, seeds, materials or soil to be protected from fungal attack with a fungicidally effective amount of the active compounds. The application can be carried out both before and after the infection of the materials, plants or seeds by the fungi.

The fungicidal compositions generally comprise between 0.1 and 95%, preferably between 0.5 and 90%, by weight of active compound.

When employed in plant protection, the amounts applied are, depending on the kind of effect desired, between 0.01 and 2.0 kg of active compound per ha.

In seed treatment, amounts of active compound of 0.001 to 0.1 g, preferably 0.01 to 0.05 g, per kilogram of seed are generally necessary.

When used in the protection of materials or stored products, the amount of active compound applied depends on the kind of application area and on the effect desired. Amounts customarily applied in the protection of materials are, for example, 0.001 g to 2 kg, preferably 0.005 g to 1 kg, of active compound per cubic meter of treated material.

The compounds I can be converted to the usual formulations, e.g. solutions, emulsions, suspensions, dusts, powders, pastes and granules. The application form depends on the respective use intended; it should in any case guarantee a fine and uniform distribution of the compound according to the invention.

The formulations are prepared in a known way, e.g. by extending the active compound with solvents and/or carriers, if desired using emulsifiers and dispersants, it being possible, when water is the diluent, also to use other organic solvents as auxiliary solvents. Suitable auxiliaries for this purpose are essentially: solvents, such as aromatics (e.g. xylene), chlorinated aromatics (e.g. chlorobenzenes), paraffins (e.g. petroleum fractions), alcohols (e.g. methanol, butanol), ketones (e.g. cyclohexanone), amines (e.g. ethanolamine, dimethylformamide) and water; carriers, such as ground natural minerals (e.g. kaolins, clays, talc, chalk) and ground synthetic ores (e.g. highly dispersed silicic acid, silicates); emulsifiers, such as nonionic and anionic emulsifiers (e.g. polyoxyethylene fatty alcohol ethers, alkylsulfonates and arylsulfonates) and dispersants, such as lignosulfite waste liquors and methylcellulose.

Suitable surfactants are alkali metal, alkaline earth metal and ammonium salts of lignosulfonic acid, naphthalenesulfonic acid, phenolsulfonic acid and dibutylnaphthalensulfonic acid, alkylarylsulfonates, alkyl sulfates, alkylsulfonates, fatty alcohol sulfates and fatty acids, and alkali metal and alkaline earth metal salts thereof, salts of sulfated fatty alcohol glycol ethers, condensation products of sulfonated naphthalene and naphthalene derivatives with formaldehyde, condensation products of naphthalene or of naphthalenesulfonic acid with phenol and formaldehyde, polyoxyethylene octylphenol ethers, ethoxylated isooctylphenol, octylphenol and nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Petroleum fractions having medium to high boiling points, such as kerosene or diesel fuel, furthermore coal tar oils, and oils of vegetable or animal origin, aliphatic, cyclic and aromatic hydrocarbons, e.g. benzene, toluene, xylene, paraffin, tetrahydronaphthalene, alkylated naphthalenes or derivatives thereof, methanol, ethanol, propanol, butanol, chloroform, carbon tetrachloride, cyclohexanol, cyclohexanone, chlorobenzene or isophorone, or highly polar solvents, e.g. dimethylformamide, dimethyl sulfoxide, N-methylpyrrolidone or water, are suitable for the preparation of directly sprayable solutions, emulsions, pastes or oil dispersions.

Powders, combinations for broadcasting and dusts can be prepared by mixing or mutually grinding the active substances with a solid carrier.

Granules, e.g. coated granules, impregnated granules and homogeneous granules, can be prepared by binding the active compounds to solid carriers. Solid carriers are, e.g., mineral earths, such as silicic acids, silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, e.g., ammonium sulfate, ammonium phosphate, ammonium nitrate or ureas, and plant products, such as cereal meal, tree bark meal, wood meal and nutshell meal, cellulose powders and other solid carriers.

The formulations generally comprise between 0.01 and 95% by weight, preferably between 0.1 and 90% by weight, of the active compound. The active compounds are employed therein in a purity of 90% to 100%, preferably 95% to 100% (according to the NMR spectrum).

EXAMPLES FOR FORMULATIONS ARE

I. 5 parts by weight of a compound according to the invention are intimately mixed with 95 parts by weight of finely divided kaolin. In this way, a dust comprising 5% by weight of the active compound is obtained.

II. 30 parts by weight of a compound according to the invention are intimately mixed with a mixture of 92 parts by weight of pulverulent silica gel and 8 parts by weight of liquid paraffin, which had been sprayed onto the surface of this silica gel. In this way, an active compound preparation with good adhesive properties (active compound content 23% by weight) is obtained.

III. 10 parts by weight of a compound according to the invention are dissolved in a mixture consisting of 90 parts by weight of xylene, 6 parts by weight of the addition product of 8 to 10 mol of ethylene oxide with 1 mol of the N-monoethanolamide of oleic acid, 2 parts by weight of the calcium salt of dodecylbenzenesulfonic acid and 2 parts by weight of the addition product of 40 mol of ethylene oxide with 1 mol of castor oil (active compound content 9% by weight).

IV. 20 parts by weight of a compound according to the invention are dissolved in a mixture consisting of 60 parts by weight of cyclohexanone, 30 parts by weight of isobutanol, 5 parts by weight of the addition product of 7 mol of ethylene oxide with 1 mol of isooctylphenol and 5 parts by weight of the addition product of 40 mol of ethylene oxide with 1 mol of castor oil (active compound content 16% by weight).

V. 80 parts by weight of a compound according to the invention are intimately mixed with 3 parts by weight of the sodium salt of diisobutylnaphthalene-α-sulfonic acid, 10 parts by weight of the sodium salt of a lignosulfonic acid from a sulfite waste liquor and 7 parts by weight of pulverulent silica gel and are ground in a hammer mill (active compound content 80% by weight).

VI. 90 parts by weight of a compound according to the invention are mixed with 10 parts by weight of N-methyl-α-pyrrolidone and a solution is obtained which is suitable for use in the form of very small drops (active compound content 90% by weight).

VII. 20 parts by weight of a compound according to the invention are dissolved in a mixture consisting of 40 parts by weight of cyclohexanone, 30 parts by weight of isobutanol, 20 parts by weight of the addition product of 7 mol of ethylene oxide with 1 mol of isooctylphenol and 10 parts by weight of the addition product of 40 mol of ethylene oxide with 1 mol of castor oil. By running the solution into 100 000 parts by weight of water and finely dispersing it therein, an aqueous dispersion is obtained comprising 0.02% by weight of the active compound.

VIII. 20 parts by weight of a compound according to the invention are intimately mixed with 3 parts by weight of the sodium salt of diisobutylnaphthalene-α-sulfonic acid, 17 parts by weight of the sodium salt of a lignosulfonic acid from a sulfite waste liquor and 60 parts by weight of pulverulent silica gel and are ground in a hammer mill. A spray emulsion comprising 0.1% by weight of the active compound is obtained by fine dispersion of the mixture in 20 000 parts by weight of water.

The active compounds can be used as such, in the form of their formulations or of the application forms prepared therefrom, e.g. in the form of directly sprayable solutions, powders, suspensions or dispersions, emulsions, oil dispersions, pastes, dusts, compositions for broadcasting or granules, by spraying, atomizing, dusting, broadcasting or watering. The application forms depend entirely on the intended uses; they should in any case guarantee the finest possible dispersion of the active compounds according to the invention.

Aqueous use forms can be prepared from emulsifiable concentrates, pastes or wettable powders (spray powders, oil dispersions) by addition of water. To prepare emulsions, pastes or oil dispersions, the substances can be homogenized in water, as such or dissolved in an oil or solvent, by means of wetting agents, tackifiers, dispersants or emulsifiers. However, concentrates comprising active substance, wetting agent, tackifier, dispersant or emulsifier and possibly solvent or oil can also be prepared, which concentrates are suitable for dilution with water.

The concentrations of active compound in the ready-for-use preparations can be varied within relatively wide ranges. In general, they are between 0.0001 and 10%, preferably between 0.01 and 1%.

The active compounds can also be used with great success in the ultra low volume (ULV) process, it being possible to apply formulations with more than 95% by weight of active compound or even the active compound without additives.

Oils of various types, herbicides, fungicides, other pesticides and bactericides can be added to the active compounds, if need be too not until immediately before use (tank mix). These agents can be added to the preparations according to the invention in a weight ratio of 1:10 to 10:1.

The preparations according to the invention can, in the application form as fungicides, also be present together with other active compounds, which e.g. with herbicides, insecticides, growth regulators, fungicides or also with fertilizers. On mixing the compounds I or the preparations comprising them in the application form as fungicides with other fungicides, in many cases an expansion of the fungicidal spectrum of activity is obtained.

The following lists of fungicides, with which the compounds according to the invention can be used in conjunction, is intended to illustrate the possible combinations but does not limit them:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate) or N,N'-polypropylenebis(thiocarbamoyl)disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenyl isopropyl carbonate or diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butyl-carbamoyl)-2-benzimidazolecarbamate, 2-(methoxy-carbonylamino)benzimidazole, 2-(2-furyl)benzimidazole, 2-(4-thiazolyl)benzimidazole, N-(1,1,2,2-tetrachloroethylthio)tetrahydrophthalimide, N-(trichloromethylthio)tetrahydrophthalimide or N-(trichloromethylthio)phthalimide, N-dichlorofluoromethylthio-N',N'-dimethyl-N-phenyl-sulfamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, 2-thiopyridine 1-oxide, 8-hydroxyquinoline or its copper salt, 2,3-dihydro-5-carboxanilido-6-methyl-1,4-oxathiin, 2,3-dihydro-5-carboxanilido-6-methyl-1,4-oxathiin 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazin-1,4-diylbis-1-(2,2,2-trichloroethyl)formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-(tert-butyl)phenyl)-2-methylpropyl]-cis-2,6-dimethylmorpholine, N-[3-(p-(tert-butyl)phenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-(n-propyl)-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene or 1,2-bis(3-methoxycarbonyl-2-thioureido)benzene, strobilurins, such as methyl E-methoxyimino[α-(o-tolyloxy)-o-tolyl]acetate, methyl E-2-{2-[6-(2-cyanophenoxy)pyrimidin-4-yloxy]phenyl}-3-methoxyacrylate, methyl-E-methoxyimino-[α-(2-phenoxyphenyl)]acetamide, methyl-E-methoxyimino[α-(2,5-dimethylphenoxy)-o-tolyl]acetamide, methyl E-2-{2-[2-trifluoromethylpyrid-6-yl]oxymethyl]phenyl}-3-methoxyacrylate, methyl (E,E)-methoxyimino{2-[1-(3-trifluoromethylphenyl)ethylideneaminooxymethyl]phenyl}acetate or methyl N-(2-{[1-(4-chlorophenyl)-1H-pyrazol-3-yl]oxymethyl}phenyl)-N-methoxycarbamate, anilinopyrimidines, such as N-(4,6-dimethylpyrimidin-2-yl)aniline, N-[4-methyl-6-(1-propynyl)pyrimidin-2-yl]aniline or N-[4-methyl-6-cyclopropylpyrimidin-2-yl]aniline, phenylpyrroles, such as 4-(2,2-difluoro-1,3-benzodioxol-4-yl)pyrrole-3-carbonitrile, cinnamamides, such as 3-(4-chlorophenyl)-3-(3,4-dimethoxyphenyl)acryloylmorpholine, and various fungicides, such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, N-(2,6-dimethylphenyl)-N-(2'-methoxyacetyl)-DL-alanine methyl ester, N-(2,6-dimethylphenyl)-N-chloroacetyl-D,L-2-aminobutyrolactone, N-(2,6-dimethylphenyl)-N-(phenylacetyl)-DL-alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoxyimino]acetamide, 1-[2-(2,4-dichlorophenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl)methyl)-1H-1,2,4-triazole, iprovalicarb, benthialiahcart, proquinazid, 5-chloro-2-cyano-4-(p-tolyl)imidazole-1-sulfonic acid dimethylamide or 3,5-dichloro-N-(3-chloro-1-ethyl-1-methyl-2-oxopropyl)-4-methylbenzamide.

SYNTHESIS EXAMPLES

The procedures described in the following synthesis examples were used to prepare further compounds I by appropriate modification of the starting materials. The compounds thus obtained are listed in the following tables, together with physical data.

Example 1

6-Chloro-5-(2,4,6-trifluorophenyl)-4-isopropylamino-2-(2-pyridyl)pyrimidine [I-1]

a) 4,6-Dihydroxy-5-(2,4,6-trifluorophenyl)-2-(2-pyridyl)pyrimidine 332 g (1.16 mol) of diethyl 2-(2,4,6-trifluorophenyl)malonate and 192 g (1.04 mol) of tributylamine were heated at 180° C. for eight hours together with 182 g (1.17 mol) of pyridine-2-carboxamidine. In the course of this, the ethanol produced was distilled off. The reaction mixture was then allowed to cool to 60-70° C. and was mixed with a solution of 116 g (2.89 mol) of sodium hydroxide in 1200 ml of water. After stirring for 30 min and cooling to approximately 20-25° C., the mixture was extracted with methyl tert-butyl ether (MTBE) and, after phase separation, the aqueous phase was acidified with 6N hydrochloric acid. After filtering off and drying, 180 g of the title compound were obtained.

$^1$H NMR: δ (ppm, $d_6$-DMSO)=8.75 (d); 8.3 (d); 8.1 (t); 7.6 (m); 7.1 (t).

b) 4,6-Dichloro-5-(2,4,6-trifluorophenyl)-2-(2-pyridyl)pyrimidine

A suspension of 80.4 g (0.252 mol) of the pyrimidine from ex. 1a in 515 g (3.36 mol) of phosphorus oxychloride was heated at 120° C. for 8 hours and then concentrated under vacuum. The residue was taken up in dichloromethane and water. After phase separation, the organic phase was dried and freed from the solvent. After chromatography on silica gel (cyclohexane/ethyl acetate), 26 g of the title compound were obtained.

¹H NMR: δ (ppm, CDCl₃)=8.9 (d); 8.6 (d); 7.8 (t); 7.5 (m); 6.8 (t).

c) 6-Chloro-5-(2,4,6-trifluorophenyl)-4-isopropylamino-2-(2-pyridyl)-pyrimidine A solution of 3.30 g (0.093 mol) of the dichloride from ex. 1b in 4.5 ml of dimethylformamide (DMF) and 2.7 g (0.046 mol) of isopropylamine was stirred at 40° C. for 24 hours. After cooling to 20-25° C., the mixture was extracted with dichloromethane and the organic phase was washed with water and saturated NaHCO₃ solution, then dried and freed from the solvent. After chromatography on silica gel (cyclohexane/ethyl acetate), 3.05 g of the title compound were obtained.

¹H NMR: δ (ppm, CDCl₃)=8.8 (d); 8.4 (d); 7.8 (t); 7.4 (dd); 6.8 (t); 4.5 (m); 4.4 (m); 1.4 (s); 1.25 (d).

TABLE I

| No. | $(R^1)_m$ | $R^2$ | $R^3$ | $R^4$ | $R^5$ | $R^6$ | $R^7$ | $R^8$ | $R^9$ | Phys. data (M.p.[° C.], ¹H NMR[ppm]; log $P_{ow}$) |
|---|---|---|---|---|---|---|---|---|---|---|
| I-1 | H | Cl | CH(CH₃)₂ | H | F | F | H | H | F | (ex. 1) |
| I-2 | H | Cl | CH₂C(=CH₂)CH₃ | CH₂CH₃ | Cl | F | H | H | H | log $P_{ow}$ 4.73 |
| I-3 | H | Cl | CH(CH₃)₂ | H | Cl | F | H | H | H | log $P_{ow}$ 3.59 |
| I-4 | H | Cl | c-C₅H₉ | H | Cl | F | H | H | H | 152-156 |
| I-5 | H | Cl | CH₂CH₃ | CH₂CH₃ | Cl | F | H | H | H | log $P_{ow}$ 4.23 |
| I-6 | H | Cl | (S) CH(CH₃)C(CH₃)₃ | H | Cl | F | H | H | H | 144-146 |
| I-7 | H | Cl | (R) CH(CH₃)C(CH₃)₃ | H | Cl | F | H | H | H | log $P_{ow}$ 4.8 |
| 1-8 | H | Cl | —(CH₂)₂—CH(CH₃)—(CH₂)₂— | | Cl | F | H | H | H | 0.9 (d, 3H); 1.1 (m, 2H); 1.6 (m, 3H); 2.9 (m, 2H); 4.1 (m, 2H); 7.1 (t, 1H); 7.4 (m, 2H); 7.8 (t, 1H); 8.4 (d, 1H); 8.9 (m, 1H) |
| 1-9 | H | Cl | CH₂CH₃ | CH₂CH₃ | F | F | H | H | F | log $P_{ow}$ 4.08 |
| 1-10 | H | Cl | (S) CH(CH₃)C(CH₃)₃ | H | F | F | H | H | F | log $P_{ow}$ 4.75 |
| I-11 | H | Cl | c-C₅H₉ | H | F | F | H | H | F | 1.4-1.7 (m, 4H); 1.8 (m, 2H); 2.1 (m, 2H); 4.6 (m, 2H); 6.9 (dd, 2H); 7.4 (m, 1H); 7.8 (t, 1H); 8.5 (d, 1H); 8.8 (d, 1H) |
| I-12 | H | Cl | (S) CH(CH₃)CF₃ | H | F | F | H | H | F | log $P_{ow}$ 4.5 |
| I-13 | H | Cl | (S) CH(CH₃)CH(CH₃)₂ | H | F | F | H | H | F | 187 |
| I-14 | H | Cl | CH₂C(CH₃)₃ | H | F | F | H | H | F | 162 |
| I-15 | H | Cl | (R) CH(CH₃)C(CH₃)₃ | H | F | F | H | H | F | 139 |
| I-16 | H | Cl | (R) CH(CH₃)CH(CH₃)₂ | H | F | F | H | H | F | 185 |
| I-17 | 6-CH₃ | Cl | CH(CH₃)₂ | H | F | F | H | H | F | 234-236 |
| I-18 | 6-CH₃ | Cl | (S) CH(CH₃)CF₃ | H | F | F | H | H | F | 238 |
| I-19 | 6-CH₃ | Cl | CH₂CH₃ | CH₂CH₃ | F | F | H | H | F | 1.0 (t, 6H); 2.7 (s, 3H); 3.4 (q, 4H); 6.8 (m, 2H); 7.3 (d, 1H); 7.7 (t, 1H); 8.2 (d, 1H) |
| I-20 | 6-CH₃ | Cl | CH₂C(CH₃)₃ | H | F | F | H | H | F | 184 |
| I-21 | 6-CH₃ | Cl | CH(CH₃)₂ | CH₃ | F | F | H | H | F | 1.1 (d, 6H); 2.55 (s, 3H); 2.7 (s, 3H); 4.8 (sept., 1H); 6.8 (dd, 2H); 7.3 (m, 1H); 7.7 (t, 1H); 8.2 (d, 1H) |
| I-22 | 6-CH₃ | Cl | CH₂CH(CH₃)₂ | CH₂CH₃ | F | F | H | H | F | 0.8 (d, 6H); 1.0 (t, 3H); 2.0 (sept., 1H); 2.7 (s, 3H); 3.2 (d, 2H); 3.3 (q, 2H); 6.8 (dd, 2H); 7.3 (d, 1H); 7.7 (t, 1H); 8.13 (d, 1H) |
| I-23 | 6-CH₃ | Cl | CH₂C(=CH₂)CH₃ | CH₂CH₃ | F | F | H | H | F | 1.1 (t, 3H); 1.45 (s, 3H); 2.7 (s, 3H); 3.4 (q, 2H); 3.9 (s, 2H); 4.8 (s, 2H); 6.75 (dd, 2H); 7.3 (m, 1H); 7.7 (t, 1H); 8.2 (d, 1H) |
| I-24 | 6-CH₃ | Cl | —(CH₂)₂—O—(CH₂)₂— | | F | F | H | H | F | log $P_{ow}$ 4.25 |
| I-25 | 6-CH₃ | Cl | CH(CH₃)CH₂CH₃ | H | F | F | H | H | F | 187 |
| I-26 | 6-CH₃ | Cl | c-C₅H₉ | H | F | F | H | H | F | 235 |
| I-27 | 6-CH₃ | Cl | (R) CH(CH₃)CH(CH₃)₂ | H | F | F | H | H | F | 171 |

TABLE I-continued

| No. | (R$^1$)$_m$ | R$^2$ | R$^3$ | R$^4$ | R$^5$ | R$^6$ | R$^7$ | R$^8$ | R$^9$ | Phys. data (M.p.[° C.], $^1$H NMR[ppm]; log P$_{ow}$) |
|---|---|---|---|---|---|---|---|---|---|---|
| I-28 | 6-CH$_3$ | Cl | —(CH$_2$)$_2$—CH(CH$_3$)—(CH$_2$)$_2$— | | F | F | H | H | F | 0.9 (d, 3H); 1.1 (m, 2H); 1.6 (m, 2H); 2.7 (s, 3H); 2.8 (m, 2H); 4.1 (m, 2H); 6.8 (t, 2H); 7.3 (m, 1H); 7.7 (t, 1H); 8.1 (d, 1H) |
| I-29 | 6-CH$_3$ | Cl | (S) CH(CH$_3$)CH(CH$_3$)$_2$ | H | F | F | H | H | F | 172 |
| I-30 | 6-CH$_3$ | Cl | (S) CH(CH$_3$)C(CH$_3$)$_3$ | H | F | F | H | H | F | 187 |
| I-31 | 6-CH$_3$ | Cl | (R) CH(CH$_3$)C(CH$_3$)$_3$ | H | F | F | H | H | F | 190 |
| I-32 | 4-CH$_3$ | Cl | (S) CH(CH$_3$)CF$_3$ | H | F | F | H | H | F | 203-205 |
| I-33 | 4-CH$_3$ | Cl | CH(CH$_3$)$_2$ | CH$_3$ | F | F | H | H | F | 195-198 |
| I-34 | 4-CH$_3$ | Cl | (S) CH(CH$_3$)CH(CH$_3$)$_2$ | H | F | F | H | H | F | 218-220 |
| I-35 | 4-CH$_3$ | Cl | —(CH$_2$)$_2$—CH(CH$_3$)—(CH$_2$)$_2$— | | F | F | H | H | F | 168-172 |
| I-36 | 4-CH$_3$ | Cl | (S) CH(CH$_3$)C(CH$_3$)$_3$ | H | F | F | H | H | F | 187-189 |
| I-37 | 4-CH$_3$ | Cl | CH$_2$CH$_3$ | CH$_2$CH$_3$ | F | F | H | H | F | 145-147 |
| I-38 | 4-CH$_3$ | Cl | CH$_2$C(CH$_3$)$_3$ | H | F | F | H | H | F | 192-5 |
| I-39 | 4-CH$_3$ | Cl | CH$_2$C(=CH$_2$)CH$_3$ | CH$_2$CH$_3$ | F | F | H | H | F | 1.1 (t, 3H); 1.5 (s, 3H); 2.45 (s, 3H); 3.4 (q, 2H); 3.9 (m, 2H); 7.8 (m, 2H); 6.8 (t, 2H); 7.2 (m, 1H); 8.2 (s, 1H); 8.7 (m, 1H) |
| I-40 | 4-CH$_3$ | Cl | CH(CH$_3$)CH$_2$CH$_3$ | H | F | F | H | H | F | 188-190 |
| I-41 | 4-CH$_3$ | Cl | c-C$_5$H$_9$ | H | F | F | H | H | F | 195-198 |
| I-42 | 4-CH$_3$ | Cl | CH(CH$_3$)$_2$ | CH$_3$ | F | F | H | H | F | 185-187 |
| I-43 | 4-CH$_3$ | Cl | —(CH$_2$)$_2$—O—(CH$_2$)$_2$— | | F | F | H | H | F | 158-162 |
| I-44 | 4-CH$_3$ | Cl | (R) CH(CH$_3$)CH(CH$_3$)$_2$ | H | F | F | H | H | F | 215-218 |
| I-45 | 4-CH$_3$ | Cl | (R) CH(CH$_3$)C(CH$_3$)$_3$ | H | F | F | H | H | F | 184-187 |
| I-46 | H | CH$_3$ | —(CH$_2$)$_2$—CH(CH$_3$)—(CH$_2$)$_2$— | | F | F | H | H | F | 112-113 |
| I-47 | H | OCH$_3$ | CH$_2$CH$_3$ | CH$_2$CH$_3$ | F | F | H | H | F | 106-108 |
| I-47-1 | H | CH$_3$ | (R)CH(CH$_3$)C(CH$_3$)$_3$ | H | F | F | H | H | F | 0.9 (s, 9H); 1.1 (d, 3H); 2.3 (s, 3H); 4.2 (m, 1H); 4.4 (m, 1H); 6.9 (t, 2H); 7.4 (m, 1H); 7.9 (m, 1H); 8.5 (d, 1H); 8.9 (m, 1H) |
| I-48 | H | CH$_3$ | (R)CH(CH$_3$)CH(CH$_3$)$_2$ | H | F | F | H | H | F | 0.9 (d, 6H); 1.1 (d, 3H); 1.8 (m, 1H); 2.3 (s, 3H); 4.2 (m, 1H); 4.4 (m, 1H); 6.9 (m, 2H); 7.4 (m, 1H); 7.8 (m, 1H); 8.4 (m, 1H); 8.8 (m, 1H) |
| I-49 | H | CH$_3$ | CH$_2$CH$_3$ | CH$_2$CH$_3$ | F | F | H | H | F | 1.0 (t, 6H); 2.3 (s, 3H); 3.4 (q, 4H); 6.8 (m, 2H); 7.4 (m, 1H); 7.8 (m, 1H); 8.4 (m, 1H); 8.8 (m, 1H) |
| I-50 | H | CH$_3$ | (S)CH(CH$_3$)CH(CH$_3$)$_2$ | H | F | F | H | H | F | 0.9 (d, 6H); 1.1 (d, 3H); 1.8 (m, 1H); 2.3 (s, 3H); 4.2 (m, 1H); 4.4 (m, 1H); 6.8 (m, 2H); 7.4 (m, 1H); 7.8 (m, 1H); 8.4 (m, 1H); 8.8 (m, 1H) |
| I-51 | H | Cl | CH(CH$_3$)CF$_3$ | H | Cl | F | H | H | H | 150 |
| I-52 | H | Cl | CH$_2$C(=CH$_2$)CH$_3$ | CH$_2$CH$_3$ | F | F | H | H | F | 1.1 (t, 3H); 1.5 (s, 3H); 3.4 (q, 2H); 3.9 (s, 2H); 4.8 (s, 2H); 6.8 (t, 2H); 7.4 (m, 1H); 7.8 (t, 1H); 8.4 (d, 1H); 8.8 (d, 1H) |
| I-53 | H | Cl | CH(CH$_3$)CH$_2$CH$_3$ | H | F | F | H | H | F | 0.9 (d, 6H); 1.1 (d, 3H); 1.8 (m, 1H); 2.3 (s, 3H); 4.2 (m, 1H); 4.4 (m, 1H); 6.9 (m, 2H); 7.4 (m, 1H); 7.8 (m, 1H); 8.4 (m, 1H); 8.8 (m, 1H) |
| I-54 | H | Cl | CH(CH$_3$)CH$_2$CH$_3$ | H | F | F | H | H | F | 172-175 |
| I-55 | H | Cl | CH(CH$_3$)$_2$ | CH$_3$ | F | F | H | H | F | 158 |
| I-56 | H | Cl | CH$_2$CF$_3$ | H | F | F | H | H | F | 200 |

TABLE I-continued

| No. | (R¹)ₘ | R² | R³ | R⁴ | R⁵ | R⁶ | R⁷ | R⁸ | R⁹ | Phys. data (M.p.[° C.], ¹H NMR[ppm]; log P_ow) |
|---|---|---|---|---|---|---|---|---|---|---|
| I-57 | H | Cl | (CH₂)₂CH(CH₃)(CH₂)₂ |  | F | F | H | H | F | 0.9 (d, 3H); 1.1 (m, 2H); 1.7 (m, 3H); 3.0 (t, 2H); 4.5 (d, 2H); 6.8 (t, 2H); 7.4 (m, 1H); 7.8 (m, 1H); 8.4 (m, 1H); 8.8 (m, 1H) |
| I-58 | H | Cl | (CH₂)₂CH(CH₃)(CH₂)₂ |  | F | F | H | H | OCH₃ | 133-135 |
| I-59 | H | Cl | CH(CH₃)₂ | H | F | F | H | H | OCH₃ | 173-175 |
| I-60 | H | Cl | (R)CH(CH₃)CH(CH₃)₂ | H | F | F | H | H | OCH₃ | 147-149 |
| I-61 | H | Cl | (R)CH(CH₃)C(CH₃)₃ | H | F | F | H | H | OCH₃ | 179-181 |
| I-62 | H | Cl | CH(CH₃)CH₂CH₃ | H | F | F | H | H | OCH₃ | 142-144 |
| I-63 | H | Cl | CH₂C(=CH₂)CH₃ | CH₂CH₃ | F | F | H | H | OCH₃ | 135-137 |
| I-64 | H | Cl | CH₂CH₃ | CH₂CH₃ | F | F | H | H | OCH₃ | logP 5.0 |
| I-65 | H | Cl | CH₂CH₃ | H | F | F | H | H | OCH₃ | logP 4.0 |
| I-66 | H | Cl | c-C₅H₉ | H | F | F | H | H | OCH₃ | 173-175 |
| I-67 | H | Cl | (S)CH(CH₃)CH(CH₃)₂ | H | F | F | H | H | OCH₃ | 145-146 |
| I-68 | H | Cl | (S)CH(CH₃)C(CH₃)₃ | H | F | F | H | H | OCH₃ | 185-187 |
| I-69 | H | Cl | (CH₂)₂CH(CH₃)(CH₂)₂ |  | F | F | H | H | OH | 185-187 |
| I-70 | H | Cl | CH(CH₃)₂ | H | F | F | H | H | OH | log.P 3.0 |
| I-71 | H | Cl | (R)CH(CH₃)CH(CH₃)₂ | H | F | F | H | H | OH | 173-175 |
| I-72 | H | Cl | (R)CH(CH₃)C(CH₃)₃ | H | F | F | H | H | OH | 175-177 |
| I-73 | H | Cl | CH₂C(=CH₂)CH₃ | CH₂CH₃ | F | F | H | H | OH | 135-137 |
| I-74 | H | Cl | (S)CH(CH₃)CH(CH₃)₂ | H | F | F | H | H | OH | 110-112 |
| I-75 | H | Cl | (S)CH(CH₃)C(CH₃)₃ | H | F | F | H | H | OH | 109-110 |
| I-76 | H | Cl | c-C₅H₉ | H | F | F | H | H | OH | 128-130 |
| I-77 | H | Cl | CH₂CH(CH₃)₂ | CH₃ | F | F | H | H | OH | 153-155 |
| I-78 | H | Cl | CH₂CH(CH₃)₂ | CH₂CH(CH₃)₂ | F | F | H | H | OH | 0.8 (d, 12H); 1.8 (m, 2H); 3.3 (m, 4H); 6.8 (d, 2H); 7.6 (m, 1H); 8.0 (m, 1H); 8.6 (d, 1H); 8.9 (m, 1H) |
| I-79 | H | Cl | CH₂CH(CH₃)₂ | CH₂CH₃ | F | F | H | H | OH | 0.8 (d, 6H); 1.0 (t, 3H); 1.9 (m, 1H); 3.3 (d, 2H); 3.5 (q, 2H); 6.8 (d, 2H); 7.6 (m, 1H); 8.0 (m, 1H); 8.6 (d, 1H); 8.9 (m, 1H) |
| I-80 | H | Cl | (CH₂)₂CH(CH₃)(CH₂)₂ |  | F | F | H | H | H | 0.9 (d, 3H); 1.1 (m, 2H); 1.7 (m, 3H); 3.0 (t, 2H); 4.5 (d, 2H); 6.8 (t, 2H); 7.5 (m, 1H); 8.0 (m, 1H); 8.5 (t, 1H); 8.8 (d, 1H); 9.4 (d, 1H) |
| I-81 | H | Cl | CH₂CH₃ | CH₂CH₃ | F | F | H | H | H | logP 4.7 |
| I-82 | H | Cl | (S)CH(CH₃)CH(CH₃)₂ | H | F | F | H | H | H | logP 5.0 |
| I-83 | H | Cl | CH(CH₃)₂ | H | F | F | H | H | H | logP 4.1 |
| I-84 | H | Cl | (R)CH(CH₃)CH(CH₃)₂ | H | F | F | H | H | H | logP 5.0 |
| I-85 | H | Cl | (CH₂)₂CH(CH₃)(CH₂)₂ |  | CH₃ | H | H | H | CH₃ | 90-94 |
| I-86 | H | Cl | CH(CH₃)₂ | H | CH₃ | H | H | H | CH₃ | 1.1 (d, 6H); 2.1 (s, 3H); 2.4 (s, 3H); 4.5 (m, 1H); 4.9 (m, 1H); 7.0 (d, 1H); 7.1 (d, 1H); 7.8 (m, 1H); 8.3 (t, 1H); 8.7 (d, 1H); 9.2 (m, 1H) |
| I-87 | H | Cl | c-C₅H₉ | H | CH₃ | H | H | H | CH₃ | 1.2 (m, 2H); 1.6 (m, 2H); 1.7 (m, 2H); 2.1 (s, 3H); 2.2 (m, 2H); 2.5 (s, 3H); 4.7 (m, 1H); 5.0 (m, 1H); 7.0 (d, 1H); 7.1 (d, 1H); 7.8 (t, 1H); 8.2 (t, 1H); 8.7 (d, 1H); 9.2 (m, 1H) |

TABLE I-continued

| No. | (R¹)ₘ | R² | R³ | R⁴ | R⁵ | R⁶ | R⁷ | R⁸ | R⁹ | Phys. data (M.p.[° C.], ¹H NMR[ppm]; log $P_{ow}$) |
|---|---|---|---|---|---|---|---|---|---|---|
| I-88 | H | Cl | (S)CH(CH₃)CH(CH₃)₂ | H | CH₃ | H | H | H | CH₃ | 0.9 (dd, 6H); 1.1 (d, 3H); 1.8 (m, 1H); 2.1 (d, 3H); 2.4 (s, 3H); 4.5 (m, 2H); 7.0 (d, 1H); 7.1 (d, 1H); 7.8 (m, 1H); 8.3 (m, 1H); 8.7 (m, 1H); 9.2 (m, 1H) |
| I-89 | H | Cl | (R)CH(CH₃)CH(CH₃)₂ | H | CH₃ | H | H | H | CH₃ | 0.9 (dd, 6H); 1.1 (d, 3H); 1.8 (m, 1H); 2.1 (d, 3H); 2.4 (5, 3H); 4.5 (m, 1H); 4.8 (m, 1H); 7.0 (d, 1H); 7.1 (m, 1H); 7.8 (m, 1H); 8.3 (m, 1H); 8.7 (m, 1H); 9.2 (m, 1H) |
| I-90 | H | Cl | CH₂CH₃ | H | CH₃ | H | H | H | CH₃ | logP 4.6 |
| I-91 | H | Cl | CH₂CH₃ | CH₂CH₃ | CH₃ | H | H | H | CH₃ | 1.0 (t, 6H); 2.0 (s, 3H); 2.4 (s, 3H); 3.4 (m, 4H); 4.5 (m, 2H); 7.1 (m, 3H); 7.4 (m, 1H); 7.8 (t, 1H); 8.4 (d, 1H); 8.8 (d, 1H) |
| I-92 | H | Cl | (R)CH(CH₃)C(CH₃)₃ | H | CH₃ | H | H | H | CH₃ | 0.8 (s, 9H); 1.1 (dd, 3H); 2.4 (s, 3H); 4.4 (m, 1H); 4.6 (t, 1H); 7.1 (m, 3H); 7.4 (m, 1H); 7.8 (t, 1H); 8.4 (d, 1H); 8.8 (m, 1H) |
| I-93 | H | Cl | (CH₂)₂CH(CH₃)(CH₂)₂ | | F | F | H | H | CN | 0.9 (d, 3H); 1.1 (m, 2H); 1.6 (m, 3H); 2.8 (m, 2H); 3.9 (m, 2H); 7.3 (m, 2H); 7.4 (m, 1H); 7.8 (m, 1H); 8.4 (d, 1H); 8.8 (m, 1H) |
| I-94 | H | Cl | CH(CH₃)₂ | H | F | H | H | H | CH₃ | logP 4.8 |
| I-95 | H | Cl | CH(CH₃)(CH₂)₂ | H | F | H | H | H | CH₃ | 1.2 (d, 3H); 1.6 (m, 2H); 1.8 (m, 2H); 2.4 (s, 3H); 3.0 (m, 2H); 4.8 (m, 1H); 7.0 (m, 3H); 7.9 (m, 1H); 8.4(q, 1H); 8.7 (d, 1H); 9.2 (m, 1H) |
| I-96 | H | Cl | (S)CH(CH₃)CH(CH₃)₂ | H | F | H | H | H | CH₃ | 0.9 (dd, 6H); 1.1 (d, 3H); 1.8 (m, 1H); 2.4 (s, 3H); 4.8 (m, 2H); 7.1 (m, 3H); 7.8 (t, 1H); 8.4 (t, 1H); 8.7 (d, 1H); 9.2 (d, 1H) |
| I-97 | H | Cl | (R)CH(CH₃)CH(CH₃)₂ | H | F | H | H | H | CH₃ | 0.9 (dd, 6H); 1.1 (d, 3H1); 1.8 (m, 1H); 2.4 (s, 3H); 4.5 (m, 1H); 4.6 (m, 1H); 7.1 (m, 3H); 7.6 (t, 1H); 8.1 (t, 1H); 8.6 (d, 1H); 9.0 (d, 1H) |
| I-98 | H | Cl | (S)CH(CH₃)C(CH₃)₃ | H | F | H | H | H | CH₃ | 0.8 (s, 9H); 1.1 (dd, 3H); 2.4 (s, 3H); 4.4 (m, 1H); 4.6 (t, 1H); 7.1 (m, 3H); 7.4 (m, 1H); 7.8 (t, 1H); 8.4 (d, 1H); 8.8 (m, 1H) |
| I-99 | H | Cl | (CH₂)₂CH(CH₃)(CH₂)₂ | | F | H | H | H | CH₃ | 172-174 |
| I-100 | H | Cl | CH(CH₃)CH₂CH₃ | H | F | H | H | H | CH₃ | 0.9 (m, 3H); 1.2 (d, 3H); 2.4 (s, 3H); 4.6 (m, 1H); 4.7 (m, 1H); 7.1 (m, 3H); 7.8 (t, 1H); 8.2 (t, 1H); 8.7 (d, 1H); 9.1 (m, 1H) |
| I-101 | H | Cl | CH₂CH₃ | CH₂CH₃ | F | H | H | H | CH₃ | 1.0 (t, 6H); 2.4 (s, 3H); 3.5 (m, 4H); 7.1 (m, 3H); 7.8 (t, 1H); 8.4 (t, 1H); 8.7 (d, 1H); 9.2 (m, 1H) |
| I-102 | H | Cl | c-C₅H₉ | H | F | H | H | H | CH₃ | 1.4(m, 2H); 1.6 (m, 4H); 2.2 (m, 2H); 4.8 (m, 2H); 7.1 (m, 3H); 7.8 (t, 1H); 8.2 (t, 1H); 8.7 (d, 1H); 9.1 (m, 1H) |
| I-103 | H | Cl | CH₂C(=CH₂)CH₃ | CH₂CH₃ | F | H | H | H | CH₃ | 1.0 (t, 3H); 1.4 (s, 3H); 2.4 (s, 3H); 3.4 (m, 2H); 3.9 (m, 2H); 4.8 (m, 2H); 7.0 (m, 2H); 7.1 (t, 1H); 7.4 (m, 1H); 7.8 (t, 1H); 8.4 (d, 1H); 8.8 (d, 1H) |
| I-104 | H | Cl | CH(CH₃)C(CH₃)₃ | H | F | H | H | H | CH₃ | 0.8 (s, 9H); 1.3 (5, 3H); 2.4 (s, 3H); 4.4 (m, 1H); 4.6 (m, 1H); 7.1 (m, 3H); 7.4 (m, 1H); 7.8 (t, 1H); 8.4 (d, 1H); 8.8 (d, 1H) |

TABLE I-continued

| No. | (R¹)ₘ | R² | R³ | R⁴ | R⁵ | R⁶ | R⁷ | R⁸ | R⁹ | Phys. data (M.p.[° C.], ¹H NMR[ppm]; log P_ow) |
|---|---|---|---|---|---|---|---|---|---|---|
| I-105 | H | Cl | CH(CH₃)₂ | H | CH₃ | H | H | H | F | 1.2 (d, 6H); 2.1 (s, 3H); 4.4 (m, 1H); 4.8 (m, 1H); 7.1 (m, 3H); 7.6 (m, 1H); 8.1 (m, 1H); 8.6 (m, 1H); 9.1 (m, 1H) |
| I-106 | H | Cl | CH(CH₃)(CH₂)₃ | H | CH₃ | H | H | H | F | 1.2 (m, 3H); 1.6 (m, 2H); 1.8 (m, 2H); 2.1 (s, 3H); 2.9 (m, 2H); 5.1 (m, 1H); 7.0 (m, 2H); 7.3 (m, 1H); 7.8 (t, 1H); 8.3 (t, 1H); 8.7 (d, 1H); 9.3 (m, 1H) |
| I-107 | H | Cl | (S)CH(CH₃)CH(CH₃)₂ | H | CH₃ | H | H | H | F | 51-52 |
| I-108 | H | Cl | (R)CH(CH₃)CH(CH₃)₂ | H | CH₃ | H | H | H | F | 0.8 (d, 6H); 1.1 (d, 3H); 1.8 (m, 1H); 2.1 (5, 3H); 4.3 (m, 2H); 7.1 (m, 3H); 7.4 (m, 1H); 7.8 (t, 1H); 8.4 (m, 1H); 8.8 (m, 1H) |
| I-109 | H | Cl | (CH₂)₂CH(CH₃)(CH₂)₂ | | CH₃ | H | H | H | F | 0.9 (d, 3H); 1.0 (m, 2H); 1.6 (m, 4H); 2.2 (s, 3H); 2.8 (t, 2H); 4.2 (m, 1H); 4.3 (m, 1H); 7.0 (m, 2H); 7.1 (m, 1H); 7.8 (t, 1H); 8.3 (t, 1H); 8.7 (d, 1H); 9.2 (m, 1H) |
| I-110 | H | Cl | CH(CH₃)CH₂CH₃ | H | CH₃ | H | H | H | F | 0.9 (t, 3H); 1.2 (d, 3H); 1.4 (m, 2H); 2.2 (s, 3H); 4.3 (m, 2H); 7.1 (m, 3H); 7.4 (m, 1H); 7.8 (t, 1H); 8.4 (d, 1H); 8.8 (m, 1H) |
| I-111 | H | Cl | CH₂CH₃ | CH₂CH₃ | CH₃ | H | H | H | F | 1.0 (t, 6H); 2.2 (s, 3H); 3.3 (m, 4H); 7.0 (m, 2H); 7.2 (m, 1H); 7.4 (m, 1H); 7.8 (t, 1H); 8.4 (d, 1H); 8.8 (m, 1H) |
| I-112 | H | Cl | c-C₅H₉ | H | CH₃ | H | H | H | F | 1.3 (m, 2H); 1.6 (m, 4H); 2.2 (m, 5H); 4.6 (m, 1H); 5.0 (m, 1H); 7.1 (m, 3H); 7,8 (t, 1H); 8,3 (t, 1H); 8.7 (d, 1H); 9.2 (m, 1H) |
| I-113 | H | Cl | (R)CH(CH₃)C(CH₃)₃ | H | CH₃ | H | H | H | F | 162-164 |
| I-114 | H | Cl | CH₂CH₃ | H | CH₃ | H | H | H | F | logP 4.1 |
| I-115 | 4-CH₃ | Cl | CH₂CH(CH₃)₂ | CH₂CH₃ | F | F | H | H | F | 0.8 (t, 6H); 1.0 (t, 3H); 2.5 (s, 3H); 3.2 (m, 2H); 3.4 (q, 2H); 6.8 (t, 2H); 7.2 (m, 1H); 8.2 (s, 1H); 8.7 (d, 1H) |
| I-116 | 3-CH₃ | Cl | (S)CH(CH₃)C(CH₃)₃ | H | F | F | H | H | F | 128-132 |
| I-117 | 3-CH₃ | Cl | CH₂CH₃ | CH₂CH₃ | F | F | H | H | F | logP 4.6 |
| I-118 | 3-CH₃ | Cl | CH₂C(CH₃)₃ | H | F | F | H | H | F | 198 |
| I-119 | 3-CH₃ | Cl | CH(CH₃)₂ | CH₃ | F | F | H | H | F | 94-96 |
| I-120 | 3-CH₃ | Cl | CH₂CH(CH₃)₂ | CH₂CH₃ | F | F | H | H | F | 0.8 (d, 6H); 1.0 (t, 3H); 1.9 (m, 1H); 2.5 (s, 3H); 3.1 (d, 2H); 3.3 (q, 2H); 6.8 (t, 2H); 7.2 (m, 1H); 7.6 (d, 1H); 8.6 (d, 1H) |
| I-121 | 3-CH₃ | Cl | CH₂C(=CH₂)CH₃ | CH₂CH₃ | F | F | H | H | F | 1.0 (t, 3H); 1.5 (s, 3H); 2.5 (s, 3H); 3.3 (q, 2H); 3.8 (s, 2H); 4.8. (d, 2H); 6.8 (t, 2H); 7.2 (m, 1H); 7.6 (d, 1H); 8.6 (d, 1H) |
| I-122 | 3-CH₃ | Cl | (CH₂)₂O(CH₂)₂ | | F | F | H | H | F | 122-127 |
| I-123 | 3-CH₃ | Cl | CH(CH₃)CH₂CH₃ | H | F | F | H | H | F | 154 |
| I-124 | 3-CH₃ | Cl | (S)CH(CH₃)CH(CH₃)₂ | H | F | F | H | H | F | 161 |
| I-125 | 3-CH₃ | Cl | (CH₂)₂CH(CH₃)(CH₂)₂ | | F | F | H | H | F | 130-132 |
| I-126 | 3-CH₃ | Cl | c-C₅H₉ | H | F | F | H | H | F | 161-163 |
| I-127 | 3-CH₃ | Cl | CH(CH₃)₂ | | F | F | H | H | F | 144-148 |
| I-128 | 3-CH₃ | Cl | (R)CH(CH₃)C(CH₃)₃ | H | F | F | H | H | F | 134-138 |

TABLE I-continued

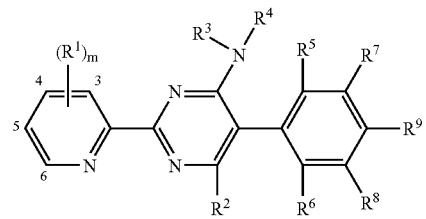

| No. | $(R^1)_m$ | $R^2$ | $R^3$ | $R^4$ | $R^5$ | $R^6$ | $R^7$ | $R^8$ | $R^9$ | Phys. data (M.p.[° C.], $^1$H NMR[ppm]; log $P_{ow}$) |
|---|---|---|---|---|---|---|---|---|---|---|
| I-129 | 3-CH$_3$ | Cl | (R)CH(CH$_3$)CH(CH$_3$)$_2$ | H | F | F | H | H | F | 159 |
| I-130 | 3-CH$_3$ | Cl | (S)CH(CH$_3$)CF$_3$ | H | F | F | H | H | F | 172 |

The determination of the lipophilicity parameter log $P_{ow}$ (Table I) was carried out in accordance with OECD test guidelines using the RP HPLC run time method.

To this end, a log k'/log $P_{ow}$ correlation curve based on ten reference substances was plotted and was validated with the help of the lipophilicity parameters of eight comparison substances established through the extraction method.

A commercially available reversed-phase C$_{18}$ stationary phase was used as stationary phase. Chromatographic separation was carried out with methanol and a buffer solution as mobile phase at pH 7.4 under isocratic conditions.

The retention times of the standards $t_R$ were converted in accordance with equation Φ into the capacity factors k', in which $t_0$, as reaction time of the solvent unretarded on the reversed-phase C$_{18}$ stationary phase, represents the dead time of the chromatographic system:

$$k' = \frac{t_R - t_0}{t_0} \Phi$$

The linear correlation of the log k' values with the log $P_{ow}$ values of the standards published in the appendix to the guidelines 92/69/EEC yields the correlation curve through linear regression.

The lipophilicity parameters log $P_{ow}$ of the analytes were after calculation of the logarithmic capacity factor log k' interpolated from the correlation curve of the standards.

The validation of the RP HPLC analytical method described and of the standards used is carried out with the help of eight comparison active compounds, the distribution behavior of which was determined with the help of the extraction method.

EXAMPLES FOR THE ACTION AGAINST HARMFUL FUNGI

The fungicidal action of the compounds of the general formula I can be demonstrated from the following tests:

The active compounds were prepared, separately or together, as a 10% emulsion in a mixture of 70% by weight of cyclohexanone, 20% by weight of Nekanil® LN (Lutensol® AP6, wetting agent with an emulsifying and dispersing action based on ethoxylated alkylphenols) and 10% by weight of Wettol® EM (nonionic emulsifier based on ethoxylated castor oil) and were appropriately diluted with water to the desired concentration.

Use Example 1

Activity Against *Alternaria solani* on Tomatoes

Leaves of pot plants of the variety "Große Fleischtomate St. Pierre" were sprayed to runoff point with an aqueous suspension prepared from a stock solution consisting of 10% of active compound, 63% of cyclohexanone and 27% of emulsifier. On the following day, the leaves were infected with an aqueous suspension of zoospores of *Alternaria solani* in 2% Biomalz solution with a concentration of 0.17×10$^6$ spores/ml. The plants were subsequently placed in a chamber saturated with water vapor at temperatures between 20 and 22° C. After 5 days, early blight in the untreated but infected control plants had so extensively developed that the infection could be visually determined in %.

In this test, the plants treated with 63 ppm of the active compounds I-1 to I-7, I-9 to I-16, I-20, I-24, I-25, I-32 and I-33, I-51, I-54, I-58, I-59, I-62, I-63, I-64, I-66, I-67, I-68 and I-94 showed a maximum of 3% infection, while the untreated plants were 100% infected.

Use Example 2

Activity Against *Botrytis cinerea* on Capsicum Leaves

Capsicum seedlings of the variety "Neusiedler Ideal Elite" were, after 4 to 5 leaves had fully developed, sprayed to runoff point with an aqueous preparation of active compound prepared from a stock solution consisting of 10% of active compound, 85% of cyclohexanone and 5% of emulsifier. The next day, the treated plants were inoculated with a spore suspension of *Botrytis cinerea* comprising 1.7×10$^6$ spores/ml in a 2% aqueous Biomalz solution. The test plants were subsequently placed in a controlled-environment chamber at 22 to 24° C. and high atmospheric humidity. After 5 days, the extent of fungal infection on the leaves could be determined visually in %.

In this test, the [lacuna] with 250 ppm of the active compounds I-1 to I-7, I-9 to I-14, I-20, I-24, I-32 to I-41 and I-43, I-51, I-53, I-55, I-56, I-57, I-58, I-59, I-62, I-63, I-64, I-66, I-67, I-68, I-82, I-83, I-86, I-87, I-88, I-90 and I-115 showed up to 5% infection, while the untreated plants were 90% infected.

Use Example 3

Protective Activity Against Powdery Mildew of Cucumber Caused by Sphaerotheca fuliginea Leaves of pot-grown cucumber seedlings of the variety "Chinesische Schlange" in the cotyledon stage were sprayed to runoff point with an aqueous preparation of active compound prepared from a stock solution consisting of 10% of active compound, 85% of cyclohexanone and 5% of emulsifier. 20 hours after the spray coating had dried on, the plants were inoculated with an aqueous suspension of spores of powdery mildew of cucumber (Sphaerotheca fuliginea). The plants were subsequently cultivated for 7 days in a greenhouse at temperatures of between 20 and 24° C. and a relative atmospheric humidity of 60 to 80%. The extent of mildew development was then determined visually in % of infection of the cotyledon area.

In this test, the [lacuna] with 63 ppm of the active compounds I-1, I-3, I-5 to I-10, I-12, I-13, I-16, I-18, I-21, I-32, I-33, I-51, I-52, I-54, I-55, I-56, I-58, I-59, I-62, I-63, I-64, I-66, I-67, I-68 and I-83 showed a maximum of 10% infection, while the untreated plants were 100% infected.

Use Example 4

Activity Against Net Blotch of Barley

Leaves of pot-grown barley seedlings of the variety "Igri" were sprayed to runoff point with an aqueous preparation of active compound prepared from a stock solution consisting of 10% of active compound, 63% of cyclohexanone and 27% of emulsifier. 24 hours after the spray coating had dried on, the leaves were inoculated with an aqueous suspension of spores of Pyrenophora [syn. Drechslera] teres, the causative agent of net blotch. The test plants were subsequently placed in a greenhouse at temperatures of between 20 and 24° C. and a relative atmospheric humidity of 95 to 100%. After 6 days, the extent of development of the disease was determined visually in % of infection of the total leaf area.

In this test, the plants treated with 63 ppm of the active compounds I-1 to I-6, I-10, I-12 to I-14, I-32, I-33, I-38, I-43, I-51, I-56, I-64 and I-86 showed not more than 15% infection, while the untreated plants were 90% infected.

TABLE I

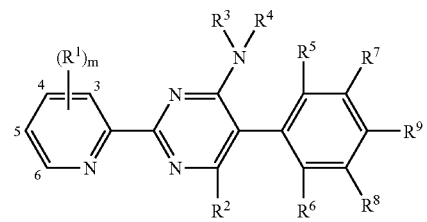

| No. | $(R^1)_m$ | $R^2$ | $R^3$ | $R^4$ | $R^5$ | $R^6$ | $R^7$ | $R^8$ | $R^9$ | Phys. data (M.p. [° C.], $^1$H-NMR [ppm]; log $P_{ow}$) |
|---|---|---|---|---|---|---|---|---|---|---|
| I-1 | H | Cl | $CH(CH_3)_2$ | H | F | F | H | H | F | (ex. 1) |
| I-2 | H | Cl | $CH_2C(=CH_2)CH_3$ | $CH_2CH_3$ | Cl | F | H | H | H | $logP_{ow}$ 4.73 |
| I-3 | H | Cl | $CH(CH_3)_2$ | H | Cl | F | H | H | H | $logP_{ow}$ 3.59 |
| I-4 | H | Cl | $c\text{-}C_5H_9$ | H | Cl | F | H | H | H | 152-156 |
| I-5 | H | Cl | $CH_2CH_3$ | $CH_2CH_3$ | Cl | F | H | H | H | $logP_{ow}$ 4.23 |
| I-6 | H | Cl | $(S)CH(CH_3)C(CH_3)_3$ | H | Cl | F | H | H | H | 144-146 |
| I-7 | H | Cl | $(R)CH(CH_3)C(CH_3)_3$ | H | Cl | F | H | H | H | $logP_{ow}$ 4.8 |
| I-8 | H | Cl | —$(CH_2)_2$—$CH(CH_3)$—$(CH_2)_2$— | | Cl | F | H | H | H | 0.9 (d, 3H); 1.1 (m, 2H); 1.6 (m, 3H); 2.9 (m, 2H); 4.1 (m, 2H); 7.1 (t, 1H); 7.4 (m, 2H); 7.8 (t, 1H); 8.4 (d, 1H); 8.9 (m, 1H) |
| I-9 | H | Cl | $CH_2CH_3$ | $CH_2CH_3$ | F | F | H | H | F | $logP_{ow}$ 4.08 |
| I-10 | H | Cl | $(S)CH(CH_3)C(CH_3)$ | H | F | F | H | H | F | $logP_{ow}$ 4.75 |
| I-11 | H | Cl | $c\text{-}C_5H_9$ | H | F | F | H | H | F | 1.4-1.7 (m, 4H); 1.8 (m, 2H); 2.1 (m, 2H); 4.6 (m, 2H); 6.9 (dd, 2H); 7.4 (m, 1H); 7.8 (t, 1H); 8.5 (d, 1H); 8.8 (d, 1H) |
| I-12 | H | Cl | $(S)CH(CH_3)CF_3$ | H | F | F | H | H | F | $logP_{ow}$ 4.5 |
| I-13 | H | Cl | $(S)CH(CH_3)CH(CH_3)_2$ | H | F | F | H | H | F | 187 |
| I-14 | H | Cl | $CH_2C(CH_3)_3$ | H | F | F | H | H | F | 162 |
| I-15 | H | Cl | $(R)CH(CH_3)C(CH_3)_3$ | H | F | F | H | H | F | 139 |
| I-16 | H | Cl | $(R)CH(CH_3)CH(CH_3)_2$ | H | F | F | H | H | F | 185 |
| I-17 | 6-$CH_3$ | Cl | $CH(CH_3)_2$ | H | F | F | H | H | F | 234-236 |
| I-18 | 6-$CH_3$ | Cl | $(S)CH(CH_3)CF_3$ | H | F | F | H | H | F | 238 |
| I-19 | 6-$CH_3$ | Cl | $CH_2CH_3$ | $CH_2CH_3$ | F | F | H | H | F | 1.0 (t, 6H); 2.7 (s, 3H); 3.4 (q, 4H); 6.8 (m, 2H); 7.3 (d, 1H); 7.7 (t, 1H); 8.2 (d, 1H) |
| I-20 | 6-$CH_3$ | Cl | $CH_2C(CH_3)_3$ | H | F | F | H | H | F | 184 |
| I-21 | 6-$CH_3$ | Cl | $CH(CH_3)_2$ | $CH_3$ | F | F | H | H | F | 1.1 (d, 6H); 2.55 (s, 3H); 2.7 (s, 3H); 4.8 (sept., 1H); 6.8 (dd, 2H); 7.3 (m, 1H); 7.7 (t, 1H); 8.2 (d, 1H) |
| I-22 | 6-$CH_3$ | Cl | $CH_2CH(CH_3)_2$ | $CH_2CH_3$ | F | F | H | H | F | 0.8 (d, 6H); 1.0 (t, 3H); 2.0 (sept., 1H); 2.7 (s, 3H); 3.2 (d, 2H); 3.3 (q, 2H); 6.8 (dd, 2H); 7.3 (d, 1H); 7.7 (t, 1H); 8.13 (d, 1H) |

TABLE I-continued

[Structure diagram: pyridine ring (with positions 3,4,5,6 labeled and (R¹)ₘ substituent) connected to a pyrimidine ring bearing R² and an NR³R⁴ group, and also connected to a phenyl ring with substituents R⁵, R⁶, R⁷, R⁸, R⁹]

| No. | (R¹)ₘ | R² | R³ | R⁴ | R⁵ | R⁶ | R⁷ | R⁸ | R⁹ | Phys. data (M.p. [° C.], ¹H-NMR [ppm]; log P_ow) |
|---|---|---|---|---|---|---|---|---|---|---|
| I-23 | 6-CH₃ | Cl | CH₂C(=CH₂)CH₃ | CH₂CH₃ | F | F | H | H | F | 1.1 (t, 3H); 1.45 (s, 3H); 2.7 (s, 3H); 3.4 (q, 2H); 3.9 (s, 2H); 4.8 (s, 2H); 6.75 (dd, 2H); 7.3 (m, 1H); 7.7 (t, 1H); 8.2 (d, 1H) |
| I-24 | 6-CH₃ | Cl | —(CH₂)₂—O—(CH₂)₂— | | F | F | H | H | F | logP_ow 4.25 |
| I-25 | 6-CH₃ | Cl | CH(CH₃)CH₂CH₃ | H | F | F | H | H | F | 187 |
| I-26 | 6-CH₃ | Cl | c-C₅H₉ | H | F | F | H | H | F | 235 |
| I-27 | 6-CH₃ | Cl | (R)CH(CH₃)CH(CH₃)₂ | H | F | F | H | H | F | 171 |
| I-28 | 6-CH₃ | Cl | —(CH₂)₂—CH(CH₃)—(CH₂)₂— | | F | F | H | H | F | 0.9 (d, 3H); 1.1 (m, 2H); 1.6 (m, 2H); 2.7 (s, 3H); 2.8 (m, 2H); 4.1 (m, 2H); 6.8 (t, 2H); 7.3 (m, 1H); 7.7 (t, 1H); 8.1 (d, 1H) |
| I-29 | 6-CH₃ | Cl | (S)CH(CH₃)CH(CH₃)₂ | H | F | F | H | H | F | 172 |
| I-30 | 6-CH₃ | Cl | (S)CH(CH₃)C(CH₃)₃ | H | F | F | H | H | F | 187 |
| I-31 | 6-CH₃ | Cl | (R)CH(CH₃)C(CH₃)₃ | H | F | F | H | H | F | 190 |
| I-32 | 4-CH₃ | Cl | (S)CH(CH₃)CF₃ | H | F | F | H | H | F | 203-205 |
| I-33 | 4-CH₃ | Cl | CH(CH₃)₂ | CH₃ | F | F | H | H | F | 195-198 |
| I-34 | 4-CH₃ | Cl | (S)CH(CH₃)CH(CH₃)₂ | H | F | F | H | H | F | 218-220 |
| I-35 | 4-CH₃ | Cl | —(CH₂)₂—CH(CH₃)—(CH₂)₂— | | F | F | H | H | F | 168-172 |
| I-36 | 4-CH₃ | Cl | (S)CH(CH₃)C(CH₃)₃ | H | F | F | H | H | F | 187-189 |
| I-37 | 4-CH₃ | Cl | CH₂CH₃ | CH₂CH₃ | F | F | H | H | F | 145-147 |
| I-38 | 4-CH₃ | Cl | CH₂C(CH₃)₃ | H | F | F | H | H | F | 192-5 |
| I-39 | 4-CH₃ | Cl | CH₂C(=CH₂)CH₃ | CH₂CH₃ | F | F | H | H | F | 1.1 (t, 3H); 1.5 (s, 3H); 2.45 (s, 3H); 3.4 (q, 2R); 3.9 (m, 2H); 7.8 (m, 2H); 6.8 (t, 2H); 7.2 (m, 1H); 8.2 (s, 1H); 8.7 (m, 1H) |
| I-40 | 4-CH₃ | Cl | CH(CH₃)CH₂CH₃ | H | F | F | H | H | F | 188-190 |
| I-41 | 4-CH₃ | Cl | c-C₅H₉ | H | F | F | H | H | F | 195-198 |
| I-42 | 4-CH₃ | Cl | CH(CH₃)₂ | CH₃ | F | F | H | H | F | 185-187 |
| I-43 | 4-CH₃ | Cl | —(CH₂)₂—O—(CH₂)₂— | | F | F | H | H | F | 158-162 |
| I-44 | 4-CH₃ | Cl | (R)CH(CH₃)CH(CH₃)₂ | H | F | F | H | H | F | 215-218 |
| I-45 | 4-CH₃ | Cl | (R)CH(CH₃)C(CH₃)₃ | H | F | F | H | H | F | 184-187 |
| I-46 | H | CH₃ | —(CH₂)₂—CH(CH₃)—(CH₂)₂— | | F | F | H | H | F | 112-113 |
| I-47 | H | OCH₃ | CH₂CH₃ | CH₂CH₃ | F | F | H | H | F | 106-108 |
| I-47-1 | H | CH₃ | (R)CH(CH₃)C(CH₃)₃ | H | F | F | H | H | F | 0.9 (s, 9H); 1.1 (d, 3H); 2.3 (s, 3H); 4.2 (m, 1H); 4.4 (m, 1H); 6.9 (t, 2H); 7.4 (m, 1H); 7.9 (m, 1H); 8.5 (d, 1H); 8.9 (m, 1H) |
| I-48 | H | CH₃ | (R)CH(CH₃)CH(CH₃)₂ | H | F | F | H | H | F | 0.9 (d, 6H); 1.1 (d, 3H); 1.8 (m, 1H); 2.3 (s, 3H); 4.2 (m, 1H); 4.4 (m, 1H); 6.9 (m, 2H); 7.4 (m, 1H); 7.8 (m, 1H); 8.4 (m, 1H); 8.8 (m, 1H) |
| I-49 | H | CH₃ | CH₂CH₃ | CH₂CH₃ | F | F | H | H | F | 1.0 (t, 6H); 2.3 (s, 3H); 3.4 (q, 4H); 6.8 (m, 2H); 7.4 (m, 1H); 7.8 (m, 1H); 8.4 (m, 1H); 8.8 (m, 1H); 0.9 (d, 6H); 1.1 (d, 3H); 1.8 (m, 1H); 2.3 (s, 3H); 4.2 (m, 1H); 4.4 (m, 1H); 6.8 (m, 2H); 7.4 (m, 1H); 7.8 (m, 1H); 8.4 (m, 1H); 8.8 (m, 1H) |
| I-50 | H | CH₃ | (S)CH(CH₃)CH(CH₃)₂ | H | F | F | H | H | F | 0.9 (d, 6H); 1.1 (d, 3H); 1.8 (m, 1H); 2.3 (s, 3H); 4.2 (m, 1H); 4.4 (m, 1H); 6.8 (m, 2H); 7.4 (m, 1H); 7.8 (m, 1H); 8.4 (m, 1H); 8.8 (m, 1H) |
| I-51 | H | Cl | CH(CH₃)CF₃ | H | Cl | F | H | H | H | 150 |
| I-52 | H | Cl | CH₂C(=CH₂)CH₃ | CH₂CH₃ | F | F | H | H | F | 1.1 (t, 3H); 1.5 (s, 3H); 3.4 (q, 2H); 3.9 (s, 2H); 4.8 (s, 2H); 6.8 (t, 2H); 7.4 (m, 1H); 7.8 (t, 1H); 8.4 (d, 1H); 8.8 (d, 1H) |

TABLE I-continued

| No. | (R¹)ₘ | R² | R³ | R⁴ | R⁵ | R⁶ | R⁷ | R⁸ | R⁹ | Phys. data (M.p. [° C.], ¹H-NMR [ppm]; log P$_{ow}$) |
|---|---|---|---|---|---|---|---|---|---|---|
| I-53 | H | Cl | CH(CH₃)CH₂CH₃ | H | F | F | H | H | F | 0.9 (d, 6H); 1.1 (d, 3H); 1.8 (m, 1H); 2.3 (s, 3H); 4.2 (m, 1H); 4.4 (m, 1H); 6.9 (m, 2H); 7.4 (m, 1H); 7.8 (m, 1H); 8.4 (m, 1H); 8.8 (m, 1H) |
| I-54 | H | Cl | CH(CH₃)CH₂CH₃ | H | F | F | H | H | F | 172-175 |
| I-55 | H | Cl | CH(CH₃)₂ | CH₃ | F | F | H | H | F | 158 |
| I-56 | H | Cl | CH₂CF₃ | H | F | F | H | H | F | 200 |
| I-57 | H | Cl | (CH₂)₂CH(CH₃)(CH₂)₂ |  | F | F | H | H | F | 0.9 (d, 3H); 1.1 (m, 2H); 1.7 (m, 3H); 3.0 (t, 2H); 4.5 (d, 2H); 6.8 (t, 2H); 7.4 (m, 1H); 7.8 (m, 1H); 8.4 (m, 1H); 8.8 (m, 1H) |
| I-58 | H | Cl | (CH₂)₂CH(CH₃)(CH₂)₂ |  | F | F | H | H | OCH₃ | 133-135 |
| I-59 | H | Cl | CH(CH₃)₂ | H | F | F | H | H | OCH₃ | 173-175 |
| I-60 | H | Cl | (R)CH(CH₃)CH(CH₃)₂ | H | F | F | H | H | OCH₃ | 147-149 |
| I-61 | H | Cl | (R)CH(CH₃)C(CH₃)₃ | H | F | F | H | H | OCH₃ | 179-181 |
| I-62 | H | Cl | CH(CH₃)CH₂CH₃ | H | F | F | H | H | OCH₃ | 142-144 |
| I-63 | H | Cl | CH₂(=CH₂)CH₃ | CH₂CH₃ | F | F | H | H | OCH₃ | 135-137 |
| I-64 | H | Cl | CH₂CH₃ | CH₂CH₃ | F | F | H | H | OCH₃ | logP 5.0 |
| I-65 | H | Cl | CH₂CH₃ | H | F | F | H | H | OCH₃ | logP 4.0 |
| I-66 | H | Cl | c-C₅H₉ | H | F | F | H | H | OCH₃ | 173-175 |
| I-67 | H | Cl | (S)CH(CH₃)CH(CH₃)₂ | H | F | F | H | H | OCH₃ | 145-146 |
| I-68 | H | Cl | (S)CH(CH₃)C(CH₃)₃ | H | F | F | H | H | OCH₃ | 185-187 |
| I-69 | H | Cl | (CH₂)₂CH(CH₃)(CH₂)₂ |  | F | F | H | H | OH | 185-187 |
| I-70 | H | Cl | CH(CH₃)₂ | H | F | F | H | H | OH | log.P 3.0 |
| I-71 | H | Cl | (R)CH(CH₃)CH(CH₃)₂ | H | F | F | H | H | OH | 173-175 |
| I-72 | H | Cl | (R)CH(CH₃)C(CH₃)₃ | H | F | F | H | H | OH | 175-177 |
| I-73 | H | Cl | CH₂C(=CH₂)CH₃ | CH₂CH₃ | F | F | H | H | OH | 135-137 |
| I-74 | H | Cl | (S)CH(CH₃)CH(CH₃)₂ | H | F | F | H | H | OH | 110-112 |
| I-75 | H | Cl | (S)CH(CH₃)C(CH₃)₃ | H | F | F | H | H | OH | 109-110 |
| I-76 | H | Cl | c-C₅H₉ | H | F | F | H | H | OH | 128-130 |
| I-77 | H | Cl | CH₂CH(CH₃)₂ | CH₃ | F | F | H | H | OH | 153-155 |
| I-78 | H | Cl | CH₂CH(CH₃)₂ | CH₂CH(CH₃)₂ | F | F | H | H | OH | 0.8 (d, 12H); 1.8 (m, 2H); 3.3 (m, 4H); 6.8 (d, 2H); 7.6 (m, 1H); 8.0 (m, 1H); 8.6 (d, 1H); 8.9 (m, 1H) |
| I-79 | H | Cl | CH₂CH(CH₃)₂ | CH₂CH₃ | F | F | H | H | OH | 0.8 (d, 6H); 1.0 (t, 3H); 1.9 (m, 1H); 3.3 (d, 2H); 3.5 (q, 2H); 6.8 (d, 2H); 7.6 (m, 1H); 8.0 (m, 1H); 8.6 (d, 1H); 8.9 (m, 1H) |
| I-80 | H | Cl | (CH₂)₂CH(CH₃)(CH₂)₂ |  | F | F | H | H | H | 0.9 (d, 3H); 1.1 (m, 2H); 1.7 (m, 3H); 3.0 (t, 2H); 4.5 (d, 2H); 6.8 (t, 2H); 7.5 (m, 1H); 8.0 (m, 1H); 8.5 (t, 1H); 8.8 (d, 1H); 9.4 (d, 1H) |
| I-81 | H | Cl | CH₂CH₃ | CH₂CH₃ | F | F | H | H | H | logP 4.7 |
| I-82 | H | Cl | (S)CH(CH₃)CH(CH₃)₂ | H | F | F | H | H | H | logP 5.0 |
| I-83 | H | Cl | CH(CH₃)₂ | H | F | F | H | H | H | logP 4.1 |
| I-84 | H | Cl | (R)CH(CH₃)CH(CH₃)₂ | H | F | F | H | H | H | logP 5.0 |
| I-85 | H | Cl | (CH₂)₂CH(CH₃)(CH₂)₂ |  | CH₃ | H | H | H | CH₃ | 90-94 |
| I-86 | H | Cl | CH(CH₃)₂ | H | CH₃ | H | H | H | CH₃ | 1.1 (d, 6H); 2.1 (s, 3H); 2.4 (s, 3H); 4.5 (m, 1H); 4.9 (m, 1H); 7.0 (d, 1H); 7.1 (d, 1H); 7.8 (m, 1H); 8.3 (t, 1H); 8.7 (d, 1H); 9.2 (m, 1H) |
| I-87 | H | Cl | c-C₅H₉ | H | CH₃ | H | H | H | CH₃ | 1.2 (m, 2H); 1.6 (m, 2H); 1.7 (m, 2H); 2.1 (s, 3H); 2.2 (m, 2H); 2.5 (s, 3H); 4.7 (m, 1H); 5.0 (m, 1H); 7.0 (d, 1H); 7.1 (d, 1H); 7.8 (t, 1H); 8.2 (t, 1H); 8.7 (d, 1H); 9.2 (m, 1H) |

TABLE I-continued

[Structure: pyridine-pyrimidine-phenyl core with substituents (R¹)ₘ on pyridine (positions 3,4,5,6), R² on pyrimidine, NR³R⁴ amino group, and R⁵, R⁶, R⁷, R⁸, R⁹ on phenyl ring]

| No. | (R¹)ₘ | R² | R³ | R⁴ | R⁵ | R⁶ | R⁷ | R⁸ | R⁹ | Phys. data (M.p. [° C.], ¹H-NMR [ppm]; log P_ow) |
|---|---|---|---|---|---|---|---|---|---|---|
| I-88 | H | Cl | (S)CH(CH₃)CH(CH₃)₂ | H | CH₃ | H | H | H | CH₃ | 0.9 (dd, 6H); 1.1 (d, 3H); 1.8 (m, 1H); 2.1 (d, 3H); 2.4 (s, 3H); 4.5 (m, 2H); 7.0 (d, 1H); 7.1 (d, 1H); 7.8 (m, 1H); 8.3 (m, 1H); 8.7 (m, 1H); 9.2 (m, 1H) |
| I-89 | H | Cl | (R)CH(CH₃)CH(CH₃)₂ | H | CH₃ | H | H | H | CH₃ | 0.9 (dd, 6H); 1.1 (d, 3H); 1.8 (m, 1H); 2.1 (d, 3H); 2.4 (s, 3H); 4.5 (m, 1H); 4.8 (m, 1H); 7.0 (d, 1H); 7.1 (m, 1H); 7.8 (m, 1H); 8.3 (m, 1H); 8.7 (m, 1H); 9.2 (m, 1H) |
| I-90 | H | Cl | CH₂CH₃ | H | CH₃ | H | H | H | CH₃ | logP 4.6 |
| I-91 | H | Cl | CH₂CH₃ | CH₂CH₃ | CH₃ | H | H | H | CH₃ | 1.0 (t, 6H); 2.0 (s, 3H); 2.4 (s, 3H); 3.4 (m, 4H); 4.5 (m, 2H); 7.1 (m, 3H); 7.4 (m, 1H); 7.8 (t, 1H); 8.4 (d, 1H); 8.8 (d, 1H) |
| I-92 | H | Cl | (R)CH(CH₃)C(CH₃)₃ | H | CH₃ | H | H | H | CH₃ | 0.8 (s, 9H); 1.1 (dd, 3H); 2.4 (s, 3H); 4.4 (m, 1H); 4.6 (t, 1H); 7.1 (m, 3H); 7.4 (m, 1H); 7.8 (t, 1H); 8.4 (d, 1H); 8.8 (m, 1H) |
| I-93 | H | Cl | (CH₂)₂CH(CH₃)(CH₂)₂ | | F | F | H | H | CN | 0.9 (m, 3H); 1.1 (m, 2H); 1.6 (m, 3H); 2.8 (m, 2H); 3.9 (m, 2H); 7.3 (m, 2H); 7.4 (m, 1H); 7.8 (m, 1H); 8.4 (d, 1H); 8.8 (m, 1H) |
| I-94 | H | Cl | CH(CH₃)₂ | H | F | H | H | H | CH₃ | logP 4.8 |
| I-95 | H | Cl | CH(CH₃)(CH₂)₂ | H | F | H | H | H | CH₃ | 1.2 (d, 3H); 1.6 (m, 2H); 1.8 (m, 2H); 2.4 (s, 3H); 3.0 (m, 2H); 4.8 (m, 1H); 7.0 (m, 3H); 7.9 (m, 1H); 8.4 (q, 1H); 8.7 (d, 1H); 9.2 (m, 1H) |
| I-96 | H | Cl | (S)CH(CH₃)CH(CH₃)₂ | H | F | H | H | H | CH₃ | 0.9 (dd, 6H); 1.1 (d, 3H); 1.8 (m, 1H); 2.4 (s, 3H); 4.8 (m, 2H); 7.1 8.7 (d, 1H); 9.2 (d, 1H) |
| I-97 | H | Cl | (R)CH(CH₃)CH(CH₃)₂ | H | F | H | H | H | CH₃ | 0.9 (dd, 6H); 1.1 (d, 3H); 1.8 (m, 1H); 2.4 (s, 3H); 4.5 (m, 1H); 4.6 (m, 1H); 7.1 (m, 3H); 7.6 (t, 1H); 8.1 (t, 1H); 8.6 (d, 1H); 9.0 (d, 1H) |
| I-98 | H | Cl | (S)CH(CH₃)C(CH₃)₃ | H | F | H | H | H | CH₃ | 0.8 (s, 9H); 1.1 (dd, 3H); 2.4 (s, 3H); 4.4 (m, 1H); 4.6 (t, 1H); 7.1 (m, 3H); 7.4 (m, 1H); 7.8 (t, 1H); 8.4 (d, 1H); 8.8 (m, 1H) |
| I-99 | H | Cl | (CH₂)₂CH(CH₃)(CH₂)₂ | | F | H | H | H | CH₃ | 172-174 |
| I-100 | H | Cl | CH(CH₃)CH₂CH₃ | H | F | H | H | H | CH₃ | 0.9 (m, 3H); 1.2 (d, 3H); 2.4 (s, 3H); 4.6 (m, 1H); 4.7 (m, 1H); 7.1 (m, 3H); 7.8 (t, 1H); 8.2 (t, 1H); 8.7 (d, 1H); 9.1 (m, 1H) |
| I-101 | H | Cl | CH₂CH₃ | CH₂CH₃ | F | H | H | H | CH₃ | 1.0 (t, 6H); 2.4 (s, 3H); 3.5 (m, 4H); 7.1 (m, 3H); 7.8 (t, 1H); 8.4 (t, 1H); 8.7 (d, 1H); 9.2 (m, 1H) |
| I-102 | H | Cl | c-C₅H₉ | H | F | H | H | H | CH₃ | 1.4 (m, 2H); 1.6 (m, 4H); 2.2 (m, 2H); 4.8 (m, 1H); 7.1 (m, 3H); 7.8 (t, 1H); 8.2 (t, 1H); 8.7 (d, 1H); 9.1 (m, 1H) |
| I-103 | H | Cl | CH₂C(=CH₂)CH₃ | CH₂CH₃ | F | H | H | H | CH₃ | 1.0 (t, 3H); 1.4 (s, 3H); 2.4 (s, 3H); 3.4 (m, 2H); 3.9 (m, 2H); 4.8 (m, 2H); 7.0 (m, 2H); 7.1 (t, 1H); 7.4 (m, 1H); 7.8 (t, 1H); 8.4 (d, 1H); 8.8 (d, 1H) |
| I-104 | H | Cl | CH(CH₃)C(CH₃)₃ | H | F | H | H | H | CH₃ | 0.8 (s, 9H); 1.3 (s, 3H); 2.4 (s, 3H); 4.4 (m, 1H); 4.6 (m, 1H); 7.1 (m, 3H); 7.4 (m, 1H); 7.8 (t, 1H); 8.4 (d, 1H); 8.8 (d, 1H) |

TABLE I-continued

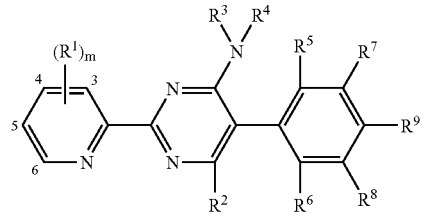

| No. | (R¹)ₘ | R² | R³ | R⁴ | R⁵ | R⁶ | R⁷ | R⁸ | R⁹ | Phys. data (M.p. [° C.], ¹H-NMR [ppm]; log P_ow) |
|---|---|---|---|---|---|---|---|---|---|---|
| I-105 | H | Cl | CH(CH₃)₂ | H | CH₃ | H | H | H | F | 1.2 (d, 6H); 2.1 (s, 3H); 4.4 (m, 1H); 4.8 (m, 1H); 7.1 (m, 38); 7.6 (m, 1H); 8.1 (m, 1H); 8.6 (m, 1H); 9.1 (m, 1H) |
| I-106 | H | Cl | CH(CH₃)(CH₂)₃ | H | CH₃ | H | H | H | F | 1.2 (m, 3H); 1.6 (m, 2H); 1.8 (m, 2H); 2.1 (s, 3H); 2.9 (m, 2H); 5.1 (m, 1H); 7.0 (m, 2H); 7.3 (m, 1H); 7.8 (t, 1H); 8.3 (t, 1H); 8.7 (d, 1H); 9.3 (m, 1H) |
| I-107 | H | Cl | (S)CH(CH₃)CH(CH₃)₂ | H | CH₃ | H | H | H | F | 51-52 |
| I-108 | H | Cl | (R)CH(CH₃)CH(CH₃)₂ | H | CH₃ | H | H | H | F | 0.8 (d, 6H); 1.1 (d, 3H); 1.8 (m, 1H); 2.1 (s, 3H); 4.3 (m, 2H); 7.1 (m, 3H); 7.4 (m, 1H); 7.8 (t, 1H); 8.4 (m, 1H); 8.8 (d, 1H) |
| I-109 | H | Cl | (CH₂)₂CH(CH₃)(CH₂)₂ |  | CH₃ | H | H | H | F | 0.9 (m, 3H); 1.0 (m, 2H); 1.6 (m, 4H); 2.2 (s, 3H); 2.8 (t, 2H); 4.2 (m, 1H); 4.3 (m, 1H); 7.0 (m, 2H); 7.1 (m, 1H); 7.8 (t, 1H); 8.3 (t, 1H); 8.7 (d, 1H); 9.2 (m, 1H) |
| I-110 | H | Cl | CH(CH₃)CH₂CH₃ | H | CH₃ | H | H | H | F | 0.9 (t, 3H); 1.2 (d, 3H); 1.4 (m, 2H); 2.2 (s, 3H); 4.3 (m, 1H); 7.1 (m, 3H); 7.4 (m, 1H); 7.8 (t, 1H); 8.4 (d, 1H); 8.8 (m, 1H) |
| I-111 | H | Cl | CH₂CH₃ | CH₂CH₃ | CH₃ | H | H | H | F | 1.0 (t, 6H); 2.2 (s, 3H); 3.3 (m, 4H); 7.0 (m, 2H); 7.2 (m, 1H); 7.4 (m, 1H); 7.8 (t, 1H); 8.4 (d, 1H); 8.8 (m, 1H) |
| I-112 | H | Cl | c-C₅H₉ | H | CH₃ | H | H | H | F | 1.3 (m, 2H); 1.6 (m, 4H); 2.2 (m, 5H); 4.6 (m, 1H); 5.0 (m, 1H); 7.1 (m, 3H); 7.8 (t, 1H); 8.3 (t, 1H); 8.7 (d, 1H); 9.2 (m, 1H) |
| I-113 | H | Cl | (R)CH(CH₃)C(CH₃)₃ | H | CH₃ | H | H | H | F | 162-164 |
| I-114 | H | Cl | CH₂CH₃ | H | CH₃ | H | H | H | F | logP 4.1 |
| I-115 | 4-CH₃ | Cl | CH₂CH(CH₃)₂ | CH₂CH₃ | F | F | H | H | F | 0.8 (t, 6H); 1.0 (t, 3H); 2.5 (s, 3H); 3.2 (m, 2H); 3.4 (q, 2H); 6.8 (t, 2H); 7.2 (m, 1H); 8.2 (s, 1H) 8.7 (d, 1H) |
| I-116 | 3-CH₃ | Cl | (S)CH(CH₃)C(CH₃)₃ | H | F | F | H | H | F | 128-132 |
| I-117 | 3-CH₃ | Cl | CH₂CH₃ | CH₂CH₃ | F | F | H | H | F | logP 4.6 |
| I-118 | 3-CH₃ | Cl | CH₂C(CH₃)₃ | H | F | F | H | H | F | 198 |
| I-119 | 3-CH₃ | Cl | CH(CH₃)₂ | CH₃ | F | F | H | H | F | 94-96 |
| I-120 | 3-CH₃ | Cl | CH₂CH(CH₃)₂ | CH₂CH₃ | F | F | H | H | F | 0.8 (d, 6H); 1.0 (t, 3H); 1.9 (m, 1H); 2.5 (s, 3H); 3.1 (d, 2H); 3.3 (q, 2H); 6.8 (t, 2H); 7.2 (m, 1H); 7.6 (d, 1H); 8.6 (d, 1H) |
| I-121 | 3-CH₃ | Cl | CH₂C(=CH₂)CH₃ | CH₂CH₃ | F | F | H | H | F | 1.0 (t, 3H); 1.5 (s, 3H); 2.5 (s, 3H); 3.3 (q, 2H); 3.8 (s, 2H); 4.8 (d, 2H); 6.8 (t, 2H); 7.2 (m, 1H); 7.6 (d, 1H); 8.6 (d, 1H) |
| I-122 | 3-CH₃ | Cl | (CH₂)₂O(CH₂)₂ |  | F | F | H | H | F | 122-127 |
| I-123 | 3-CH₃ | Cl | CH(CH₃)CH₂CH₃ | H | F | F | H | H | F | 154 |
| I-124 | 3-CH₃ | Cl | (S)CH(CH₃)CH(CH₃)₂ | H | F | F | H | H | F | 161 |
| I-125 | 3-CH₃ | Cl | (CH₂)₂CH(CH₃)(CH₂)₂ |  | F | F | H | H | F | 130-132 |
| I-126 | 3-CH₃ | Cl | c-C₅H₉ | H | F | F | H | H | F | 161-163 |
| I-127 | 3-CH₃ | Cl | CH(CH₃)₂ |  | F | F | H | H | F | 144-148 |
| I-128 | 3-CH₃ | Cl | (R)CH(CH₃)C(CH₃)₃ | H | F | F | H | H | F | 134-138 |
| I-129 | 3-CH₃ | Cl | (R)CH(CH₃)CH(CH₃)₂ | H | F | F | H | H | F | 159 |
| I-130 | 3-CH₃ | Cl | (S)CH(CH₃)CF₃ | H | F | F | H | H | F | 172 |

We claim:

1. A 2-(2-pyridyl)-5-phenyl-6-aminopyrimidine of the formula I,

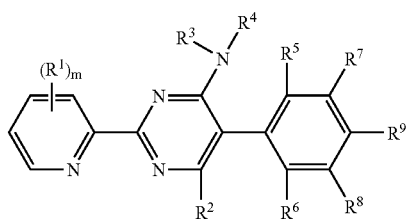

wherein:

$R^1$ is halogen, hydroxyl, cyano, oxo, nitro, amino, mercapto, $C_1$-$C_6$-alkyl, $C_1$-$C_6$-haloalkyl, $C_2$-$C_6$-alkenyl, $C_2$-$C_6$-alkynyl, $C_3$-$C_6$-cycloalkyl, $C_1$-$C_6$-alkoxy, $C_1$-$C_6$-haloalkoxy, carboxyl, $C_1$-$C_7$-alkoxycarbonyl, carbamoyl, $C_1$-$C_7$-alkylaminocarbonyl, $C_1$-$C_6$-alkyl-$C_1$-$C_6$-alkylaminocarbonyl, morpholinocarbonyl, pyrrolidinocarbonyl, $C_1$-$C_7$-alkylcarbonylamino, $C_1$-$C_6$-alkylamino, di($C_1$-$C_6$-alkyl)amino, $C_1$-$C_6$-alkylthio, $C_1$-$C_6$-alkylsulfinyl, $C_1$-$C_6$-alkylsulfonyl, hydroxysulfonyl, aminosulfonyl, $C_1$-$C_6$-alkylaminosulfonyl or di($C_1$-$C_6$-alkyl)aminosulfonyl;

m is 0, 1, 2, 3 or 4;

$R^2$ is halogen, cyano, $C_1$-$C_6$-alkyl, $C_1$-$C_6$-haloalkyl, $C_1$-$C_6$-alkoxy, $C_1$-$C_6$-haloalkoxy or $C_3$-$C_6$-alkenyloxy;

$R^3$, $R^4$ independently of one another, are hydrogen, $C_1$-$C_6$-alkyl, $C_1$-$C_6$-haloalkyl, $C_3$-$C_6$-cycloalkyl, $C_3$-$C_6$-halocycloalkyl, $C_2$-$C_6$-alkenyl, $C_2$-$C_6$-haloalkenyl, $C_3$-$C_6$-cycloalkenyl, $C_2$-$C_6$-alkynyl, $C_2$-$C_6$-haloalkynyl or $C_3$-$C_6$-cycloalkynyl, or $R^3$ and $R^4$ can also, together with the nitrogen atom to which they are bonded, form a five- or six-membered ring which may be interrupted by an atom from the group consisting of O, N and S and/or may carry one or more substituents from the group consisting of halogen, $C_1$-$C_6$-alkyl, $C_1$-$C_6$-haloalkyl or oxy-$C_1$-$C_3$-alkylenoxy or in which two adjacent carbon atoms or one N— and one neighboring carbon atom can be connected via a $C_1$-$C_4$-alkylene chain;

$R^5$ is halogen, $C_1$-$C_6$-alkyl or $C_1$-$C_6$-haloalkyl;

$R^6$ is hydrogen or one of the groups mentioned under $R^5$;

$R^7$, $R^8$ independently of one another, are hydrogen, halogen, $C_1$-$C_6$-alkyl or $C_1$-$C_6$-haloalkyl;

$R^9$ is hydrogen, halogen, hydroxyl, cyano, $C_1$-$C_6$-alkyl, $C_1$-$C_6$-alkoxy, $C_3$-$C_6$-cycloalkoxy, $C_1$-$C_6$-haloalkoxy, $C_1$-$C_6$-alkoxycarbonyl or $C_1$-$C_6$-alkylaminocarbonyl.

2. A compound as claimed in claim 1, wherein m is zero or 1, 2 or 3 and $R^1$ has the following meaning:

halogen, hydroxyl, cyano, nitro, amino, mercapto, $C_1$-$C_6$-alkyl, $C_1$-$C_6$-haloalkyl, $C_2$-$C_6$-alkenyl, $C_2$-$C_6$-alkynyl, $C_3$-$C_6$-cycloalkyl, $C_1$-$C_6$-alkoxy, $C_1$-$C_6$-haloalkoxy, carboxyl, $C_1$-$C_7$-alkoxycarbonyl, carbamoyl, $C_1$-$C_7$-alkylaminocarbonyl, $C_1$-$C_6$-alkyl-$C_1$-$C_6$-alkylaminocarbonyl, morpholinocarbonyl, pyrrolidinocarbonyl, $C_1$-$C_7$-alkylcarbonylamino, $C_1$-$C_6$-alkylamino, di($C_1$-$C_6$-alkyl)amino, $C_1$-$C_6$-alkylthio, $C_1$-$C_6$-alkylsulfinyl, $C_1$-$C_6$-alkylsulfonyl, hydroxysulfonyl, aminosulfonyl, alkylaminosulfonyl or di($C_1$-$C_6$-alkyl)aminosulfonyl.

3. A compound as claimed in claim 1, wherein:

$R^2$ is halogen, $C_1$-$C_6$-alkyl or $C_1$-$C_6$-alkoxy;

$R^3$, $R^4$ independently of one another, are hydrogen, $C_1$-$C_6$-alkyl, $C_1$-$C_6$-haloalkyl, $C_3$-$C_6$-cycloalkyl or $C_2$-$C_6$-alkenyl; or $R^3$ and $R^4$ can also, together with the nitrogen atom to which they are bonded, form a five- or six-membered ring which may be interrupted by an oxygen atom or may carry a $C_1$-$C_6$-alkyl substituent;

$R^5$, $R^6$ independently of one another, are halogen;

$R^7$, $R^8$ independently of one another, are halogen;

$R^9$ is hydrogen, halogen, hydroxyl, $C_1$-$C_6$-alkoxy or $C_1$-$C_6$-alkoxycarbonyl.

4. A compound as claimed in claim 1, wherein $R^2$ is chlorine.

5. A compound as claimed in claim 1, wherein the combination of the substituents $R^5$ to $R^9$ has the following meanings: 2-methyl-4-fluoro; 2-fluoro-4-methyl; 2,4-dimethyl; 2-chloro-6-fluoro; 2,6-difluoro; 2,6-dichloro; 2-methyl-6-fluoro; 2,4,6-trifluoro; 2,6-difluoro-4-methoxy or pentafluoro.

6. A compound as claimed in claim 1, wherein:

$R^1$ is propyl;
$R^2$ is chlorine;
$R^3$ is ethyl;
$R^4$ is hydrogen;
$R^5$ is fluorine;
$R^6$ is chlorine;
$R^7$, $R^8$ and $R^9$ are hydrogen.

7. A process for the preparation of a 5-phenylpyridine as claimed in claim 1 in which $R^2$ is chlorine, which comprises reacting a 2-pyridylamidine of the formula II,

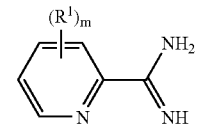

with a phenylmalonate of the formula III,

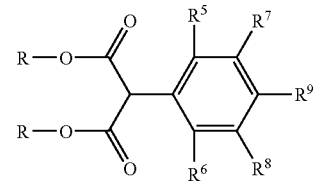

in which R is $C_1$-$C_6$-alkyl, to give a compound of the formula IV,

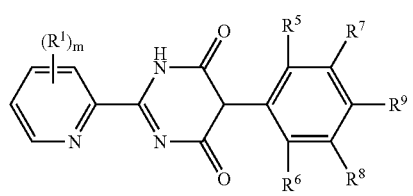

which is converted by a chlorinating agent to a dichloro-pyrimidine of the formula V

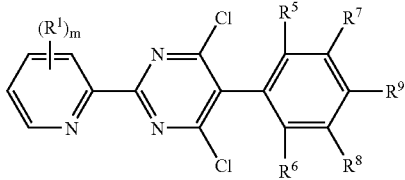
(V)

which is converted, with an amine of the formula VI

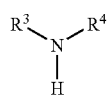
(VI)

to a pyrimidine derivative of claim 1 in which $R^2$ is chlorine.

8. A process for the preparation of a 5-phenylpyridine as claimed in claim 1 in which $R^2$ is $C_1$-$C_6$-alkyl or $C_1$-$C_6$-haloalkyl, which comprises reacting a 2-pyridylamidine of the formula II

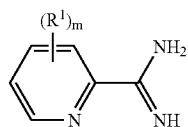
(II)

with a phenyl-b-ketoester of the formula VII,

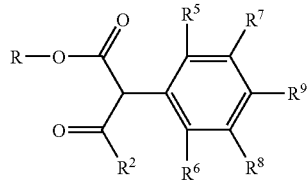
(VII)

in which R is $C_1$-$C_6$-alkyl, to give a compound of the formula IVa

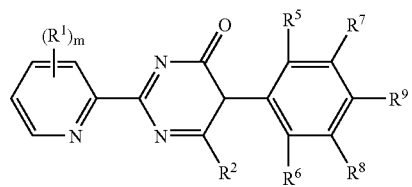
(IVa)

which is converted by a chlorinating agent to a chloro-pyrimidine of the formula Va

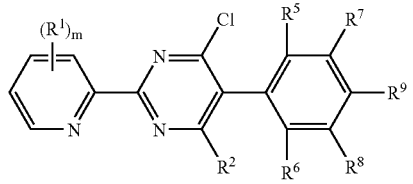
(Va)

which is converted, with an amine of formula VI, (VI)

to a pyrimidine derivative of claim 1 in which $R^2$ is $C_1$-$C_6$-alkyl or $C_1$-$C_6$-haloalkyl.

9. The process of claim 7 further comprising adding N,N-dimethylformamide, or a nitrogenous base to the reaction converting formula IV to formula V.

10. The process of claim 8 further comprising adding N,N-dimethylformamide, or a nitrogenous base to the reaction converting formula IVa to formula Va.

11. The process of claim 7 further comprising conducting the reaction of converting formula II to formula IV in the presence of a base.

12. The process of claim 8 further comprising conducting the reaction of converting II to IVa in the presence of a base.

13. The process of claim 9 further comprising using an amount of said base in excess of stoichiometric amounts.

14. The process of claim 10 further comprising using an amount of said base in excess of stoichiometric amounts.

15. The process of claim 11 further comprising using an amount of said base in excess of stoichiometric amounts.

16. The process of claim 12 further comprising using an amount of said base in excess of stoichiometric amounts.

17. An intermediate of the formula IV (IV)

or V,

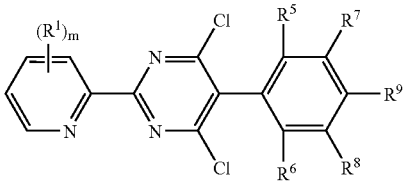
(V)

wherein $R^1$ is halogen, hydroxyl, cyano, oxo, nitro, amino, mercapto, $C_1$-$C_6$-alkyl, $C_1$-$C_6$-haloalkyl, $C_2$-$C_6$-alkenyl, $C_2$-$C_6$-alkynyl, $C_3$-$C_6$-cycloalkyl, $C_1$-$C_6$-alkoxy, $C_1$-$C_6$-haloalkoxy, carboxyl, $C_1$-$C_7$-alkoxycarbonyl, carbamoyl, $C_1$-$C_7$-alkylaminocarbonyl, $C_1$-$C_6$-alkyl-$C_1$-$C_6$-alkylaminocarbonyl, morpholinocarbonyl, pyrrolidinocarbonyl, $C_1$-$C_1$-alkylcarbonylamino, $C_1$-$C_6$-alkylamino, di($C_1$-$C_6$-alkyl)amino, $C_1$-$C_6$-alkylthio, $C_1$-$C_6$-alkylsulfinyl, $C_1$-$C_6$-alkylsulfonyl, hydroxysulfonyl, aminosulfonyl, $C_1$-$C_6$-alkylaminosulfonyl or di($C_1$-$C_6$-alkyl)aminosulfonyl; m is 0,1, 2, 3 or 4; and the combination of the substituents $R^5$ to $R^9$ has the following meanings: $R^5$=methyl, $R^6,R^7,R^8$=H and $R^9$=fluoro; $R^5$=fluoro, $R^6,R^7,R^8$=H and $R^9$=methyl; $R^5,R^9$=methyl and $R^6,R^7,R^8$=H; $R^5$=chloro, $R^6$=fluoro and $R^7,R^8,R^9$=H; $R^5,R^6$=fluoro and $R^7,R^8,R^9$=H; $R^5,R^6$=chloro and $R^7,R^8,R^9$=H; $R^5$=methyl, $R^6$=fluoro and $R^7,R^8,R^9$=H; $R^5,R^6,R^9$=fluoro and $R^7,R^8$=H; $R^5,R^6$=fluoro, $R^9$=methoxy and $R^7,R^8$—H; or $R^5,R^6,R^7,R^8,R^9$=fluoro.

18. An intermediate of the formula IVa

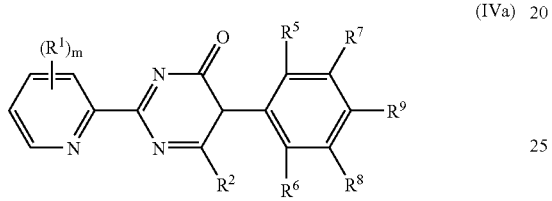
(IVa)

or Va,

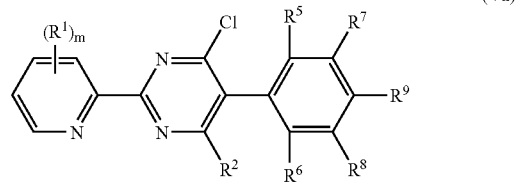
(Va)

wherein $R^1$ is halogen, hydroxyl, cyano, oxo, nitro, amino, mercapto, $C_1$-$C_6$-alkyl, $C_1$-$C_6$-haloalkyl, $C_2$-$C_6$-alkenyl, $C_2$-$C_6$-alkynyl, $C_3$-$C_6$-cycloalkyl, $C_1$-$C_6$-alkoxy, $C_1$-$C_6$-haloalkoxy, carboxyl, $C_1$-$C_7$-alkoxycarbonyl, carbamoyl, $C_1$-$C_7$-alkylaminocarbonyl, $C_1$-$C_6$-alkyl-$C_1$-$C_6$-alkylaminocarbonyl, morpholinocarbonyl, pyrrolidinocarbonyl, $C_1$-$C_7$-alkylcarbonylamino, $C_1$-$C_6$-alkylamino, di($C_1$-$C_6$-alkyl)amino, $C_1$-$C_6$-alkylthio, $C_1$-$C_6$-alkylsulfinyl, $C_1$-$C_6$-alkylsulfonyl, hydroxysulfonyl, aminosulfonyl, $C_1$-$C_6$-alkylaminosulfonyl or di($C_1$-$C_6$-alkyl)aminosulfonyl; m is 0, 1, 2, 3 or 4; $R^2$ is C1-C6-alkyl or $C_1$-$C_6$-haloalkyl; and the combination of the substituents $R^5$ to $R^9$ has the following meanings: $R^5$=methyl, $R^6,R^7,R^8$=H and $R^9$=fluoro; $R^5$=fluoro, $R^6,R^7,R^8$=H and $R^9$=methyl; $R^5,R^9$=methyl and $R^6,R^7,R^8$=H; $R^5$=chloro, $R^6$=fluoro and $R^7,R^8,R^9$=H; $R^5,R^6$=fluoro and $R^7,R^8,R^9$=H; $R^5,R^6$=chloro and $R^7,R^8,R^9$=H; $R^5$=methyl, $R^6$=fluoro and $R^7,R^8,R^9$=H; $R^5,R^6,R^9$=fluoro and $R^7,R^8$=H; $R^5,R^6$=fluoro, $R^9$=methoxy and $R^7,R^8$—H; or $R^5,R^6,R^7,R^8,R^9$=fluoro.

19. A composition suitable for the control of harmful phytopathogenic fungi, comprising a carrier and a compound of claim 1.

20. The composition of claim 19 wherein said carrier is a solid carrier.

21. The composition of claim 19 wherein said carrier is a liquid carrier.

22. A method for the control of harmful phytopathogenic fungi, which comprises treating the fungi or the materials, plants, ground or seeds to be protected from fungal attack with an effective amount of a compound of claim 1.

* * * * *